(12) United States Patent
May et al.

(10) Patent No.: US 9,999,624 B2
(45) Date of Patent: *Jun. 19, 2018

(54) COMBINATION ALZHEIMER THERAPY USING ANTI-N3PGLU ABETA ANTIBODIES + A BACE INHIBITOR

(71) Applicant: Eli Lilly and Company, Indianapolis, IN (US)

(72) Inventors: Patrick Cornelious May, Carmel, IN (US); Dustin James Mergott, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/503,027

(22) PCT Filed: Sep. 8, 2015

(86) PCT No.: PCT/US2015/048807
§ 371 (c)(1),
(2) Date: Feb. 10, 2017

(87) PCT Pub. No.: WO2016/043997
PCT Pub. Date: Mar. 24, 2016

(65) Prior Publication Data
US 2017/0224702 A1    Aug. 10, 2017

Related U.S. Application Data

(60) Provisional application No. 62/050,967, filed on Sep. 16, 2014.

(51) Int. Cl.
| | |
|---|---|
| A61K 39/395 | (2006.01) |
| A61K 31/542 | (2006.01) |
| C07K 16/18 | (2006.01) |
| C07D 513/04 | (2006.01) |
| A61K 45/06 | (2006.01) |
| A61K 39/00 | (2006.01) |

(52) U.S. Cl.
CPC ........ A61K 31/542 (2013.01); A61K 39/3955 (2013.01); A61K 45/06 (2013.01); C07D 513/04 (2013.01); C07K 16/18 (2013.01); A61K 2039/505 (2013.01); C07K 2317/24 (2013.01)

(58) Field of Classification Search
CPC .............. A61K 31/542; A61K 39/3955; A61K 2039/505; A61K 45/06; C07K 16/18; C07D 513/04

See application file for complete search history.

(56) References Cited

U.S. PATENT DOCUMENTS

| | | | |
|---|---|---|---|
| 8,158,620 B2 | 4/2012 | Suzuki et al. | |
| 8,278,334 B2 | 10/2012 | Cumming et al. | |
| 8,338,407 B2 | 12/2012 | Hall et al. | |
| 8,592,408 B2 | 11/2013 | Hall et al. | |
| 8,841,293 B1 | 9/2014 | Green et al. | |
| 8,940,734 B2 | 1/2015 | Hall et al. | |
| 8,961,972 B2 | 2/2015 | Lu et al. | |
| 8,987,254 B2 | 3/2015 | Green et al. | |
| 2013/0142806 A1* | 6/2013 | Lu ......................... | C07K 16/18 424/142.1 |
| 2014/0275044 A1* | 9/2014 | Green ................... | A61K 31/542 514/224.2 |

OTHER PUBLICATIONS

Jacobsen, et al., "Combined Treatment with a Bace Inhibitor and Anti-A1 Antibody Gantenerumab Enhances Amyloid Reduction in App Mice", Journal of Neuroscience 34(35) (2014) pp11621-11630.
May, et al., "Robust Central Reduction of Amyloid- in Humans with an Orally Available, Non-Peptidic -Secretase Inhibitor", Journal of Neuroscience 31(46) (2011) pp16507-16516.
Demattos, et al., "Combination Therapy with a Plaque Specific Ao Antibody and Bace Inhibitor Results in Dramatic Plaque Lowering in Aged Pdapp Transgenic Mice", Jul. 16, 2014.
Alzforum, "Anti-Amyloid Therapies Combine Forces to Knock Out Plaques", Jul. 25, 2014.

* cited by examiner

*Primary Examiner* — Kimberly Ballard
(74) *Attorney, Agent, or Firm* — Nelsen L. Lentz

(57) ABSTRACT

The present invention provides a method of treating a cognitive or neurodegenerative disease, comprising administering to a patient in need of such treatment an effective amount of a compound of the formula I, or a pharmaceutically acceptable salt thereof; in combination with an effective amount of an anti-N3pGlu Abeta monoclonal antibody.

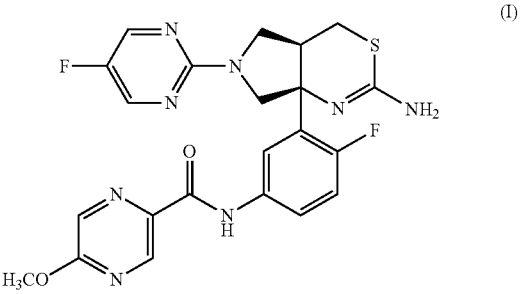

(I)

15 Claims, No Drawings

SEQUENCE LISTING

<160> NUMBER OF SEQ ID NOS: 14

<210> SEQ ID NO 1
<211> LENGTH: 16
<212> TYPE: PRT
<213> ORGANISM: Artificial Sequence
<220> FEATURE:
<223> OTHER INFORMATION: Synthetic Construct

<400> SEQUENCE: 1

Lys Ser Ser Gln Ser Leu Leu Tyr Ser Arg Gly Lys Thr Tyr Leu Asn
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Ala Val Ser Lys Leu Asp Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Val Gln Gly Thr His Tyr Pro Phe Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Gly Tyr Asp Phe Thr Arg Tyr Tyr Ile Asn
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Gly Tyr Thr Phe Thr Arg Tyr Tyr Ile Asn
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Synthetic Construct

<400> SEQUENCE: 6

Trp Ile Asn Pro Gly Ser Gly Asn Thr Lys Tyr Asn Glu Lys Phe Lys
1               5                   10                  15

Gly

<210> SEQ ID NO 7
<211> LENGTH: 6
<212> TYPE: PRT
<213> ORGANISM: Artificial Sequence
<220> FEATURE:
<223> OTHER INFORMATION: Synthetic Construct

<400> SEQUENCE: 7

Glu Gly Ile Thr Val Tyr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Glu Gly Thr Thr Val Tyr
1               5

<210> SEQ ID NO 9
<211> LENGTH: 112
<212> TYPE: PRT
<213> ORGANISM: Artificial Sequence
<220> FEATURE:
<223> OTHER INFORMATION: Synthetic Construct

<400> SEQUENCE: 9

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Leu Leu Gln Lys Pro Gly Gln Ser
        35                  40                  45

Pro Gln Leu Leu Ile Tyr Ala Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

<210> SEQ ID NO 10
<211> LENGTH: 115
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Thr Arg Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
            50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Thr Val Tyr Trp Gly Gln Gly Thr Thr Val Thr
            100                 105                 110

Val Ser Ser
        115

<210> SEQ ID NO 11
<211> LENGTH: 115
<212> TYPE: PRT
<213> ORGANISM: Artificial Sequence
<220> FEATURE:
<223> OTHER INFORMATION: Synthetic Construct

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Thr Val Tyr Trp Gly Gln Gly Thr Thr Val Thr
            100                 105                 110

Val Ser Ser
        115

<210> SEQ ID NO 12
<211> LENGTH: 219
<212> TYPE: PRT
<213> ORGANISM: Artificial Sequence
<220> FEATURE:
<223> OTHER INFORMATION: Synthetic Construct

<400> SEQUENCE: 12

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Leu Leu Gln Lys Pro Gly Gln Ser
        35                  40                  45

Pro Gln Leu Leu Ile Tyr Ala Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

```
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 13
<211> LENGTH: 444
<212> TYPE: PRT
<213> ORGANISM: Artificial Sequence
<220> FEATURE:
<223> OTHER INFORMATION: Synthetic Construct

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Thr Arg Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Thr Val Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
                435                 440

<210> SEQ ID NO 14
<211> LENGTH: 444
<212> TYPE: PRT
<213> ORGANISM: Artificial Sequence
<220> FEATURE:
<223> OTHER INFORMATION: Synthetic Construct

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Tyr
                20                  25                  30

Tyr Ile Asn Trp Val Arg Gln Ala Pro Gly Gln Gly Leu Glu Trp Met
            35                  40                  45

Gly Trp Ile Asn Pro Gly Ser Gly Asn Thr Lys Tyr Asn Glu Lys Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Thr Val Tyr Trp Gly Gln Gly Thr Thr Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

```
Leu Tyr Ser Leu Ser Ser Val Val Thr Val Pro Ser Ser Leu Gly
            180             185             190

Thr Gln Thr Tyr Ile Cys Asn Val Asn His Lys Pro Ser Asn Thr Lys
        195             200             205

Val Asp Lys Lys Val Glu Pro Lys Ser Cys Asp Lys Thr His Thr Cys
210             215             220

Pro Pro Cys Pro Ala Pro Glu Leu Leu Gly Gly Pro Ser Val Phe Leu
225             230             235             240

Phe Pro Pro Lys Pro Lys Asp Thr Leu Met Ile Ser Arg Thr Pro Glu
                245             250             255

Val Thr Cys Val Val Val Asp Val Ser His Glu Asp Pro Glu Val Lys
            260             265             270

Phe Asn Trp Tyr Val Asp Gly Val Glu Val His Asn Ala Lys Thr Lys
        275             280             285

Pro Arg Glu Glu Gln Tyr Asn Ser Thr Tyr Arg Val Val Ser Val Leu
    290             295             300

Thr Val Leu His Gln Asp Trp Leu Asn Gly Lys Glu Tyr Lys Cys Lys
305             310             315             320

Val Ser Asn Lys Ala Leu Pro Ala Pro Ile Glu Lys Thr Ile Ser Lys
                325             330             335

Ala Lys Gly Gln Pro Arg Glu Pro Gln Val Tyr Thr Leu Pro Pro Ser
            340             345             350

Arg Asp Glu Leu Thr Lys Asn Gln Val Ser Leu Thr Cys Leu Val Lys
        355             360             365

Gly Phe Tyr Pro Ser Asp Ile Ala Val Glu Trp Glu Ser Asn Gly Gln
    370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
                405             410             415

Gln Gly Asn Val Phe Ser Cys Ser Val Met His Glu Ala Leu His Asn
            420             425             430

His Tyr Thr Gln Lys Ser Leu Ser Leu Ser Pro Gly
        435             440
```

COMBINATION ALZHEIMER THERAPY USING ANTI-N3PGLU ABETA ANTIBODIES + A BACE INHIBITOR

The present invention relates to a combination of a BACE inhibitor with an anti-N3pGlu Abeta monoclonal antibody, and to methods of using the same to treat certain neurological disorders, such as Alzheimer's disease.

The present invention is in the field of treatment of Alzheimer's disease and other diseases and disorders involving amyloid β (Abeta) peptide, a neurotoxic and highly aggregatory peptide segment of the amyloid precursor protein (APP). Alzheimer's disease is a devastating neurodegenerative disorder that affects millions of patients worldwide. In view of the currently approved agents on the market which afford only transient, symptomatic benefits to the patient, there is a significant unmet need in the treatment of Alzheimer's disease.

Alzheimer's disease is characterized by the generation, aggregation, and deposition of Abeta in the brain. Complete or partial inhibition of beta-secretase (beta-site amyloid precursor protein-cleaving enzyme; BACE) has been shown to have a significant effect on plaque-related and plaque-dependent pathologies in mouse models. This suggests that even small reductions in Abeta peptide levels might result in a long-term significant reduction in plaque burden and synaptic deficits, thus providing significant therapeutic benefits, particularly in the treatment of Alzheimer's disease.

Moreover, antibodies that specifically target N3pGlu Abeta have been shown to lower plaque level in vivo (US 2013/0142806). N3pGlu Abeta, also referred to as N3pE or Abeta$_{p3-42}$, is a truncated form of the Abeta peptide found only in plaques. Although N3pGlu Abeta peptide is a minor component of the deposited Abeta in the brain, studies have demonstrated that N3pGlu Abeta peptide has aggressive aggregation properties and accumulates early in the deposition cascade.

A combination of a BACE inhibitor with an antibody that binds N3pGlu Abeta peptide is desired to provide treatment for Abeta peptide-mediated disorders, such as Alzheimer's disease, which may be more effective than either drug alone. For example, treatment with such combination may allow for use of lower doses of either or both drugs as compared to each drug used alone, potentially leading to lower side effects while maintaining efficacy. It is believed that targeting the removal of deposited forms of Abeta with an N3pG antibody and a BACE inhibitor will facilitate the phagocytic removal of pre-existing plaque deposits while at the same time reduce or prevent further deposition of Abeta by inhibiting the generation of Abeta.

US 2009/0209755 discloses fused aminodihydrothiazine derivatives which possess BACE inhibitory activity and are further disclosed as useful therapeutic agents for a neurodegenerative disease caused by Aβ peptide, such as Alzheimer's type dementia. In addition, *J. Neuroscience*, 31(46), pages 16507-16516 (2011) discloses (S)-4-(2,4-difluoro-5-pyrimidin-5-yl-phenyl)-4-methyl-5,6-dihydro-4H-[1,3]thiazin-2-ylamine, an orally administered CNS-active BACE inhibitor. U.S. Pat. No. 8,278,334 discloses a method of treating a cognitive or neurodegenerative disease comprising administering a substituted cyclic amine BACE-1 inhibitor with an anti-amyloid antibody. Further, *J. Neuroscience*, 34(35), pages 11621-11630 (2014) discloses that combined treatment with a BACE inhibitor and an anti-abeta antibody Gentenerumab enhances amyloid reduction in APP$_{London}$ mice.

Accordingly, the present invention provides a method of treating a cognitive or neurodegenerative disease, comprising administering to a patient in need of such treatment an effective amount of a BACE inhibitor in combination with an effective amount of an anti-N3pGlu Abeta monoclonal antibody.

More specifically, the present invention provides a method of treating a cognitive or neurodegenerative disease, comprising administering to a patient in need of such treatment an effective amount of a compound of Formula I:

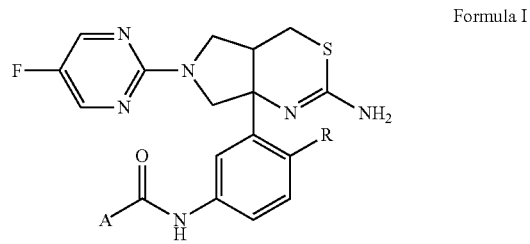

Formula I wherein R is H or F; and
A is:

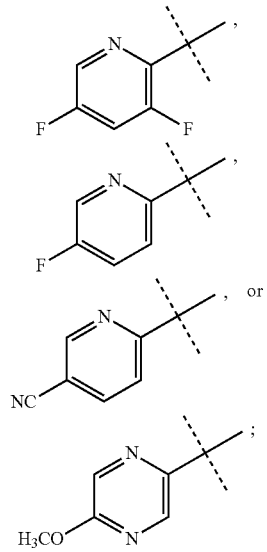

or a pharmaceutically acceptable salt thereof; in combination with an effective amount of an anti-N3pGlu Abeta monoclonal antibody.

The present invention also provides a method of treating a disease that is characterized by the formation and deposition of Abeta, comprising administering to a patient in need of such treatment an effective amount of a compound of Formula I, or a pharmaceutically acceptable salt thereof, in combination with an effective amount of an anti-N3pGlu Abeta monoclonal antibody.

The present invention further provides a method of treating Alzheimer's disease, comprising administering to a patient in need of such treatment an effective amount of a compound of Formula I, or a pharmaceutically acceptable salt thereof, in combination with an effective amount of an anti-N3pGlu Abeta monoclonal antibody.

The present invention also provides a method of treating mild Alzheimer's disease, comprising administering to a patient in need of such treatment an effective amount of a compound of Formula I, or a pharmaceutically acceptable salt thereof, in combination with an effective amount of an anti-N3pGlu Abeta monoclonal antibody.

The present invention further provides a method of treating mild cognitive impairment, comprising administering to a patient in need of such treatment an effective amount of a compound of Formula I, or a pharmaceutically acceptable salt thereof, in combination with an effective amount of an anti-N3pGlu Abeta monoclonal antibody.

The present invention further provides a method of treating prodromal Alzheimer's disease, comprising administering to a patient in need of such treatment an effective amount of a compound of Formula I, or a pharmaceutically acceptable salt thereof, in combination with an effective amount of an anti-N3pGlu Abeta monoclonal antibody.

In addition, the present invention provides a method for the prevention of the progression of mild cognitive impairment to Alzheimer's disease, comprising administering to a patient in need of such treatment an effective amount of a compound of Formula I, or a pharmaceutically acceptable salt thereof, in combination with an effective amount of an anti-N3pGlu Abeta monoclonal antibody.

The present invention further provides a method of treating cerebral amyloid angiopathy (CAA), comprising administering to a patient in need of such treatment an effective amount of a compound of Formula I, or a pharmaceutically acceptable salt thereof, in combination with an effective amount of an anti-N3pGlu Abeta monoclonal antibody.

Furthermore, the present invention provides a compound of Formula I or a pharmaceutically acceptable salt thereof, in combination with an effective amount of an anti-N3pGlu Abeta monoclonal antibody, for use in therapy, in particular for the treatment of Alzheimer's disease, mild Alzheimer's disease, prodromal Alzheimer's disease or for the prevention of the progression of mild cognitive impairment to Alzheimer's disease.

The invention further provides a pharmaceutical composition, comprising a compound of Formula I, or a pharmaceutically acceptable salt thereof, with one or more pharmaceutically acceptable carriers, diluents, or excipients, in combination with a pharmaceutical composition of an anti-N3pGlu Abeta monoclonal antibody, with one or more pharmaceutically acceptable carriers, diluents, or excipients.

In addition, the invention provides a kit, comprising a compound of Formula I, or a pharmaceutically acceptable salt thereof, and an anti-N3pGlu Abeta monoclonal antibody. The invention further provides a kit, comprising a pharmaceutical composition, comprising a compound of Formula I, or a pharmaceutically acceptable salt thereof, with one or more pharmaceutically acceptable carriers, diluents, or excipients, and a pharmaceutical composition, comprising an anti-N3pGlu Abeta monoclonal antibody with one or more pharmaceutically acceptable carriers, diluents, or excipients. As used herein, a "kit" includes separate containers of each component, wherein one component is a compound of Formula I, or a pharmaceutically acceptable salt thereof, and another component is an anti-N3pGlu Abeta monoclonal antibody, in a single package. A "kit" may also include separate containers of each component, wherein one component is a compound of Formula I, or a pharmaceutically acceptable salt thereof, and another component is an anti-N3pGlu Abeta monoclonal antibody, in separate packages with instructions to administer each component as a combination.

The invention further provides the use of a combination of a compound of the Formula I, or a pharmaceutically acceptable salt thereof, and an effective amount of an anti-N3pGlu Abeta monoclonal antibody, for the manufacture of a medicament for the treatment of Alzheimer's disease, mild Alzheimer's disease, prodromal Alzheimer's disease or for the prevention of the progression of mild cognitive impairment to Alzheimer's disease.

One of ordinary skill in the art will appreciate and recognize that "anti-N3pGlu Abeta monoclonal antibody", and the specific antibodies, "B12L" and "R17L" are identified and disclosed along with methods for making and using said antibodies by one of ordinary skill in the art, in U.S. Pat. No. 8,679,498 B2, entitled "Anti-N3pGlu Amyloid Beta Peptide Antibodies and Uses Thereof", issued Mar. 25, 2014 (U.S. Ser. No. 13/810,895). See for example Table 1 of U.S. Pat. No. 8,679,498 B2.

In addition, amino acid sequences for certain antibodies used in the present invention are provided below in Table A:

TABLE A

| | Antibody SEQ ID NOs | | | |
|---|---|---|---|---|
| Antibody | Light Chain | Heavy Chain | LCVR | HCVR |
| B12L | 12 | 13 | 9 | 10 |
| R17L | 12 | 14 | 9 | 11 |

A cognitive or neurodegenerative disease includes Alzheimer's disease, mild Alzheimer's disease, mild cognitive impairment, prodromal Alzheimer's disease, cerebral amyloid angiopathy (CAA), Down's syndrome, and the like.

As used herein, the terms "treating", "to treat", or "treatment", includes restraining, slowing, stopping, reducing, or reversing the progression or severity of an existing symptom, disorder, condition, or disease.

As used herein, the term "patient" refers to a human.

The term "inhibition of production of Abeta peptide" is taken to mean decreasing of in vivo levels of Abeta peptide in a patient.

As used herein, the term "effective amount" refers to the amount or dose of compound of Formula I, or a pharmaceutically acceptable salt thereof, and to the amount or dose of an anti-N3pGlu Abeta monoclonal antibody which, upon single or multiple dose administration to the patient, provides the desired effect in the patient under diagnosis or treatment. It is understood that the combination therapy of the present invention is carried out by administering a compound of Formula I, or a pharmaceutically acceptable salt thereof, together with the anti-N3pGlu Abeta monoclonal antibody in any manner which provides effective levels of the compound of Formula I and the anti-N3pGlu Abeta monoclonal antibody in the body.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of Formula I and pharmaceutically acceptable salts thereof are generally effective over a wide dosage range in the combination of the present invention. For example, dosages per day normally fall within the range of about 0.1 mg/day to about 1000 mg/day, preferably about 0.1 mg/day to about 500 mg/day, and most preferably about 0.1 mg/day to about 100 mg/day. In addition, the anti-N3pGlu Abeta monoclonal antibody is generally effective over a wide dosage range in the combination of the present invention. For example, dosages per week normally fall within the range of about 0.1 to 10 mg/kg/week, preferably about 0.3 to about 6 mg/kg/week, and most preferably about 0.3 mg/kg/week to about 3 mg/kg/week. In some instances dosage levels below the lower limit of the aforesaid ranges may be more than adequate, while in other cases still larger doses may be employed with acceptable side effects, and therefore the above dosage range is not intended to limit the scope of the invention in any way.

The BACE inhibitors and the antibodies of the present invention are preferably formulated as pharmaceutical compositions administered by any route which makes the compound bioavailable. The route of administration may be varied in any way, limited by the physical properties of the drugs and the convenience of the patient and the caregiver. Preferably, anti-N3pGlu Abeta monoclonal antibody compositions are for parenteral administration, such as intravenous or subcutaneous administration. In addition, the BACE inhibitor, such as the compound of Formula I, or pharmaceutically acceptable salt thereof, is for oral, parenteral, or transdermal administration, including intravenous or subcutaneous administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

As used herein, the phrase "in combination with" refers to the administration of the BACE inhibitor, such as a compound of Formula I, or a pharmaceutically acceptable salt thereof, with an anti-N3pGlu Abeta monoclonal antibody, such as an anti-N3pGlu Abeta monoclonal antibody simultaneously, or sequentially in any order, or any combination thereof. The two molecules may be administered either as part of the same pharmaceutical composition or in separate pharmaceutical compositions. The BACE inhibitor can be administered prior to, at the same time as, or subsequent to administration of the anti-N3pGlu Abeta monoclonal antibody, or in some combination thereof. Where the anti-N3pGlu Abeta monoclonal antibody is administered at repeated intervals (e.g. during a standard course of treatment), the BACE inhibitor can be administered prior to, at the same time as, or subsequent to, each administration of the anti-N3pGlu Abeta monoclonal antibody, or some combination thereof, or at different intervals in relation to therapy with the anti-N3pGlu Abeta monoclonal antibody, or in a single or series of dose(s) prior to, at any time during, or subsequent to the course of treatment with the anti-N3pGlu Abeta monoclonal antibody.

The following paragraphs describe preferred groups, substituents, and configurations of the present invention.

Preferred compounds are:
N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide; and
N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-3,5-difluoro-pyridine-2-carboxamide; and the pharmaceutically acceptable salts thereof.

N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide, or a pharmaceutically acceptable salt thereof is especially preferred.

N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide is most preferred.

Furthermore, crystalline Form 2 N-[3-[(4aR,7aS)-2-Amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide is a preferred compound; and crystalline Form 2 N-[3-[(4aR,7aS)-2-Amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide, characterized by a substantial peak in the X-ray diffraction spectrum, at diffraction angle 2-theta of 11.8°, with one or more peaks selected from the group consisting of 18.6°, 19.3°, and 26.7°; with a tolerance for the diffraction angles of 0.2 degrees is especially preferred.

Preferred anti-N3pGlu Abeta monoclonal antibodies are B12L and R17L which are identified in U.S. Pat. No. 8,679,498 B2 (See for example Table 1 therein), with B12L being especially preferred.

One of ordinary skill in the art will appreciate that compounds of Formula I can exist in tautomeric forms, as depicted in Scheme A. When any reference in this application to one of the specific tautomers of the compound of Formula I is given, it is understood to encompass both tautomeric forms and all mixtures thereof.

Scheme A

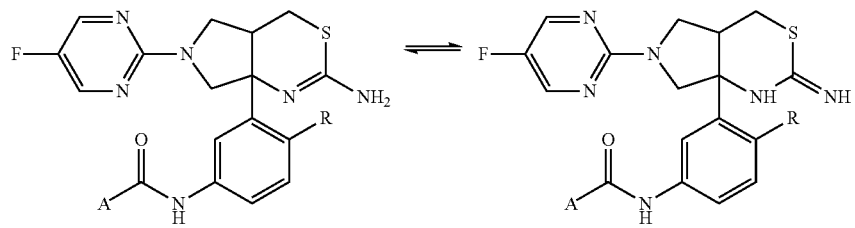

Certain stereochemical centers have been left unspecified and certain substituents have been eliminated in the following schemes for the sake of clarity and are not intended to limit the teaching of the schemes in any way. Furthermore, individual isomers, enantiomers, and diastereomers may be separated or resolved by one of ordinary skill in the art at any convenient point in the synthesis of compound of Formula I by methods such as selective crystallization techniques or chiral chromatography (See for example, J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples.

One of ordinary skill in the art will appreciate that compounds of the invention are comprised of a core that contains at least two chiral centers:

Scheme B

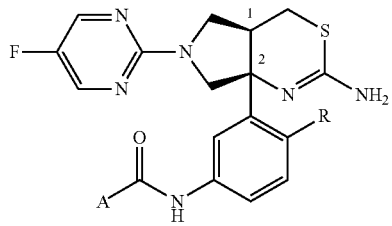

Although the present invention contemplates all individual enantiomers, as well as mixtures of the enantiomers of said compounds, including racemates, the compounds with the absolute configuration at the carbon atoms labeled 1 and 2 as illustrated in Scheme B are preferred compounds of the invention.

Additionally, certain intermediates described in the following schemes may contain one or more nitrogen protecting groups. The variable protecting group may be the same or different in each occurrence depending on the particular reaction conditions and the particular transformations to be performed. The protection and deprotection conditions are well known to the skilled artisan and are described in the literature (See for example "Greene's Protective Groups in Organic Synthesis", Fourth Edition, by Peter G. M. Wuts and Theodora W. Greene, John Wiley and Sons, Inc. 2007).

Compounds of Formula I, or pharmaceutically acceptable salts thereof, may be prepared by a variety of procedures known in the art, some of which are illustrated in the Preparations and Examples below. The specific synthetic steps for each of the routes described may be combined in different ways, or in conjunction with steps from different procedures, to prepare compounds of Formula I, or salts thereof. The products of each step can be recovered by conventional methods well known in the art, including extraction, evaporation, precipitation, chromatography, filtration, trituration, and crystallization. In addition, all substituents unless otherwise indicated, are as previously defined. The reagents and starting materials are readily available to one of ordinary skill in the art.

As used herein, "APP" refers to amyloid precursor protein; "BOC" refers to tert-butoxycarbonyl; "BSA" refers to Bovine Serum Albumin; "CSF" refers to cerebrospinal fluid; "DCC" refers to 1,3-dicyclohexylcarbodiimide; "DIC" refers to diisopropylcarbodiimide; "DCM" refers to dichloromethane; "DIPEA" refers to diisopropylethylamine "DMAP" refers to dimethylaminopyridine; "DMEM" refers to Dulbecco's Modified Eagle's Medium; "DMSO" refers to dimethylsulfoxide; "EDCI" refers to 1-(3-dimethylaminopropyl)-3-ethylcarbodiimide hydrochloride; "EDTA" refers to ethylenediaminetetraacetic acid; "ee" refers to enantiomeric excess; "EtOAc" refers to ethyl acetate; "Ex" refers to example; "F12" refers to Ham's F12 medium; "FBS" refers to Fetal Bovine Serum; "FRET" refers to fluorescence resonance energy transfer; "HATU" refers to (dimethylamino)-N,N-dimethyl(3H-[1,2,3]triazolo[4,5-b]pyridin-3-yloxy)methaniminium hexafluorophosphate; "HEK" refers to human embryonic kidney; "hr refers to hour or hours; "HOAc" refers to acetic acid; "HOAt" refers to 1-hydroxy-7-azobenzotriazole; "HOBt" refers to 1-hydroxylbenzotriazole hydrate; "HBTU" refers to refers to 2-(1H-benzotriazole-1-yl)-1,1,3,3-tetramethyluronium hexafluorophosphate; "HRP" refers to Horseradish Peroxidase; "$IC_{50}$" refers to the concentration of an agent that produces 50% of the maximal inhibitory response possible for that agent; "iPr" refers to isopropyl; "min" refers to minute or minutes; "MTBE" refers to methyl tert-butyl ether; "PBS" refers to Phosphate Buffered Saline; "PDAPP" refers to platelet derived amyloid precursor protein; "Prep" refers to preparation; "psi" refers to pounds per square inch; "PyBOP" refers to benzotriazol-1-yloxytripyrrolidino-phosphonium hexafluorophosphate; "PyBrop" refers to bromo-tris-pyrrolidino phosphoniumhexafluoro phosphate; "RFU" refers to relative fluorescence unit "$R_t$" refers to retention time; "SCX" refers to strong cation exchange chromatography; "SFC" refers to supercritical fluid chromatography; "SEM" refers to standard error of the mean; "THF" refers to tetrahydrofuran and "TMB" refers to 3,3',5,5'-teramethylbenzidine.

The following preparations and examples further illustrate the invention.

In the schemes below, all substituents unless otherwise indicated, are as previously defined. The reagents and starting materials are generally readily available to one of ordinary skill in the art. Others may be made by standard techniques of organic and heterocyclic chemistry using the procedures described in the Preparations and Examples which follow including any novel procedures.

Scheme 1

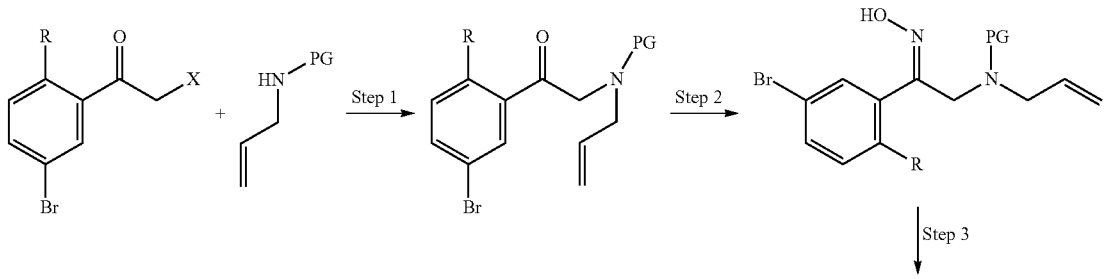

-continued

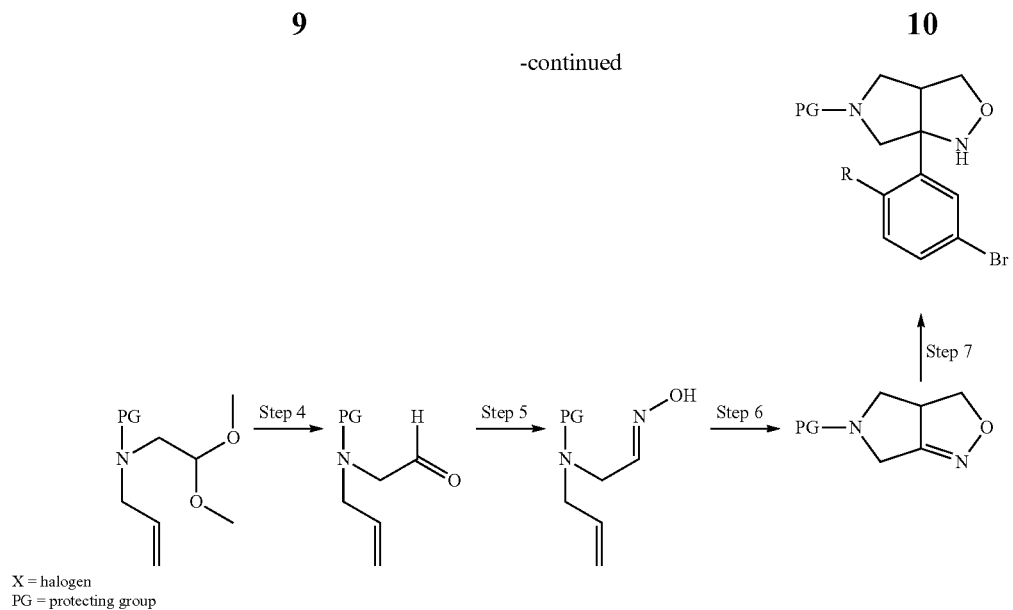

X = halogen
PG = protecting group

Scheme 1 depicts the formation of oximes (product of Step 2) and (product of Step 5). The oximes can each be used to form the bicyclic isoxazole (product of Steps 3 or 7). The substituted aromatic group can be inserted at different points of the synthesis as shown in Scheme 1, Step 1 and Step 7. "PG" is a protecting group developed for the amino group, such as carbamates and allyl. Such groups are well known and appreciated in the art.

In a 2-step reaction, a ketone with a beta halogen can be alkylated (Step 1) with a protected allyl amine using an inorganic base such as potassium carbonate and then treated with hydroxylamine hydrochloride and an organic base such as pyridine in a polar protic solvent such as ethanol to give the oxime (Step 2). The oxime product of Step 2 can then be converted to the bicyclic isoxazole in a 3+2 cyclization by several methods such as heating the oxime of Step 2 in a non-polar solvent such as toluene or xylenes to form the bicyclic isoxazole (Step 3). Alternatively, an oxime can be formed starting from a dimethyl acetal which is treated with an acid such as formic acid to form the aldehyde (product of Step 4). In step 5, the aldehyde of Step 4 can then be converted to the oxime product of Step 5 with hydroxylamine hydrochloride and a base such as sodium acetate trihydrate. The bicyclic isoxazole product of Step 6 can be formed from the oxime as shown in Step 6 using an aqueous solution of sodium hypochlorite. In step 7, the protected bicyclic isoxazole is then reacted with an aromatic organolithium reagent or Grignard reagent to give protected bicyclic isoxazole product of Step 7.

Scheme 2

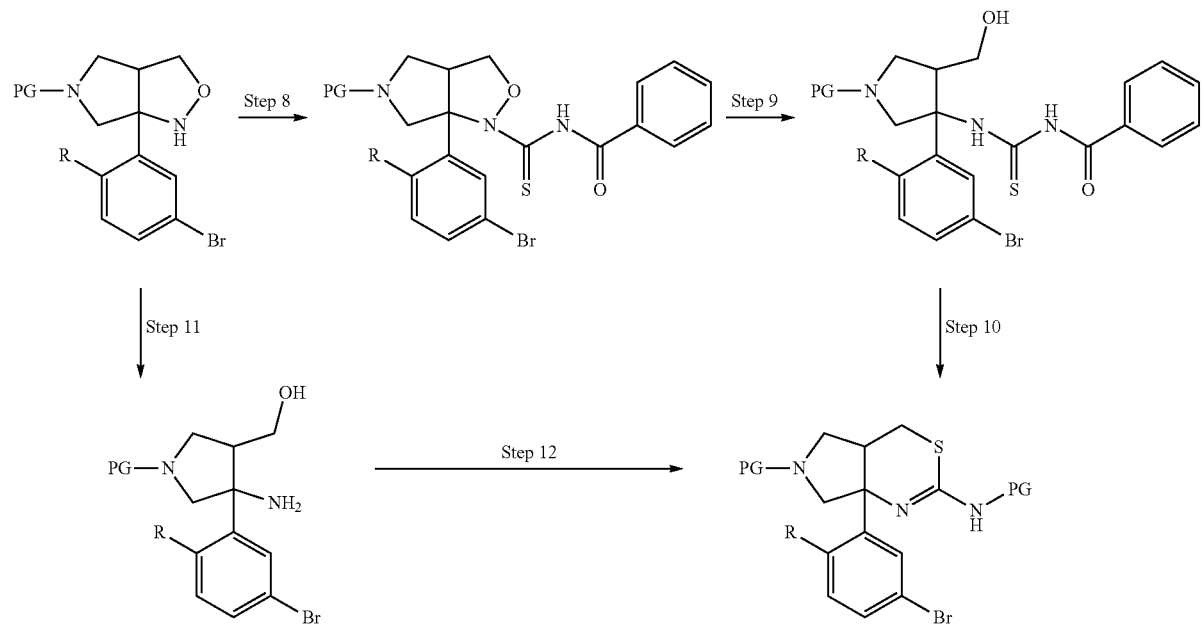

Scheme 2 illustrates different routes to the protected pyrrolo thiazine product of Step 10 or Step 12. The protected bicyclic isoxazole can be treated with powdered Zn in acetic acid or by Raney Nickel in a polar solvent such as ethanol under pressure hydrogenation conditions to give an aminopyrrolidine methanol (product of Step 11). The aminopyrrolidine methanol product of Step 11 is then reacted with benzoyl isothiocyanate in a polar solvent such as THF followed by the addition of 1,1carbonyldiimidazole (CDI) to give the fused protected pyrrolidine thiazine (product of Step 12). Alternatively, the amine of the bicyclic isoxazole can be reacted with benzoyl isothiocyanate to give the thiourea (product of Step 8), and then, in Step 9 the isoxazole ring can be opened with powdered zinc in acetic acid to give the hydroxyl compound product of Step 9. The hydroxyl compound can then be treated with CDI in a polar aprotic solvent such as THF or 1-chloro-N,N,2-trimethylpropenylamine in DCM to form the fused protected pyrrolidine thiazine (product of Step 10). The fused pyrrolidine thiazine can also be formed from a Mitsunobu reaction such as using triphenylphosphine and diisopropyl azodicarboxylate (DIAD).

Scheme 3

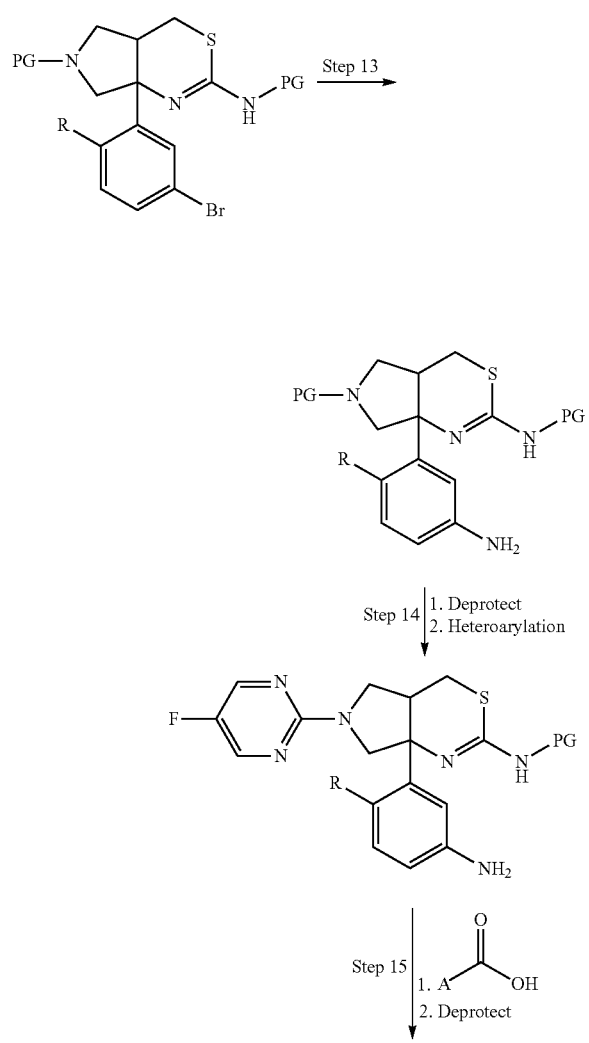

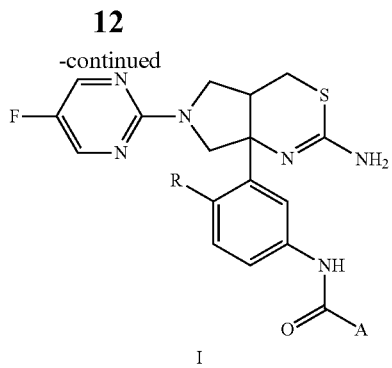

Scheme 3 depicts the conversion of the pyrrolo thiazine to the aniline (product of Step 13) which can then be acylated followed by the deprotection and heteroarylation of the pyrrolidine. Acylation of the aniline nitrogen and deprotection of the thiazine amine leads to compounds of Formula I.

Azido-dehalogenation is performed on the appropriate pyrrolo thiazine in the presence of an azide source, such as sodium azide. Such azido-dehalogenation reactions are well known and appreciated in the art. Reduction of the resulting azide intermediate to the aniline (product of Step 13) may be effected by hydrogenation conditions that are well known and described in the art or by reducing agents well known in the art, such as $LiAlH_4$, $NaBH_4$, and $PPh_3$.

A BOC protected pyrrolidine can be deprotected under acidic conditions well known in the art (Step 1 of Step 14). The deprotected pyrrolidine can then be heteroarylated in a nucleophilic aromatic substitution (SNAr) with a substituted aromatic pyrimidine using an organic base such as dipea, triethylamine, or N,N,N,N'-tetramethylguanidine to give the product of Step 2 in Step 14. The aniline product of Step 14 can be coupled with heteroaromatic carboxylic acids under coupling conditions (product of Step 1 of Step 15). One skilled in the art will recognize that there are a number of methods and reagents for amide formation resulting from the reaction of carboxylic acids and amines. For example, the reaction of an appropriate aniline with an appropriate acid in the presence of a coupling reagent and an amine base such as DIPEA or triethylamine, will give a compound of Formula I following deprotection of the thiazine amine. Coupling reagents include carbodiimides such as DCC, DIC, EDCI, and aromatic oximes such as HOBt and HOAt. Additionally, uronium or phosphonium salts of non-nucleophilic anions such as HBTU, HATU, PyBOP, and PyBrOP can be used in place of the more traditional coupling reagents. Additives such as DMAP may be used to enhance the reaction. Alternatively, the protected aniline amine can be acylated using substituted benzoyl chlorides in the presence of a base such as triethylamine or pyridine. The protected thiazine amine can then be deprotected with an organic base such as pyridine and methylhydroxylamine hydrochloride in a polar aprotic solvent such as ethanol or an inorganic base such as lithium hydroxide in methanol to give compounds of Formula I.

In an optional step, a pharmaceutically acceptable salt of a compound of Formula I can be formed by reaction of an appropriate free base of Formula I with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One of ordinary skill in the art will appreciate that a compound of Formula I is readily converted to and may be isolated as a pharmaceutically acceptable salt, such as a hydrochloride salt.

PREPARATIONS AND EXAMPLES

The following preparations and examples further illustrate the invention.

Preparation 1

1-(3-Bromophenyl)-2-(diallylamino)ethanone

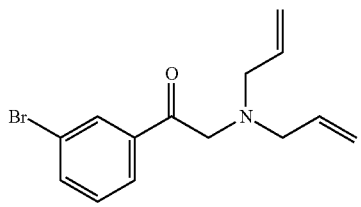 [SMILES: C=CCN(CC=C)CC(=O)c1cccc(Br)c1]

Potassium carbonate (38.8 g, 281 mmol) is added to 3-bromophenacyl bromide (60 g 216 mmol) in acetonitrile (430 mL), and the mixture is cooled under nitrogen to 0° C. Diallylamine (34.6 mL, 280.63 mmol) is added drop wise over 1 hour and the reaction is allowed to warm to 22° C. overnight. The crude reaction mixture is concentrated and the residue is partitioned in water (300 mL) and MTBE (300 mL). The aqueous layer is discarded and the organic layer is washed with water (100 mL, 2×) and with brine (100 mL). The organic layer is dried over sodium sulfate, filtered, and the solvent evaporated to constant weight to give the title compound (62 g, 98%). ES/MS (m/e): 294 (M+1).

Preparation 2

Benzyl N-(2,2-dimethoxyethyl)carbamate

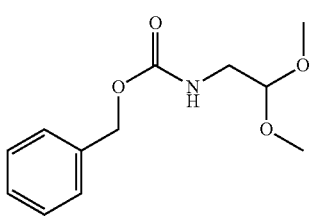 [SMILES: COC(CNC(=O)OCc1ccccc1)OC]

A solution of aminoacetaldehyde dimethyl acetal (25 mL, 229 mmol) in toluene (120 mL) is treated at 0° C. with a 4.85 M sodium hydroxide solution (70.8 mL, 343.5 mmol). The mixture is stirred at 0° C. for 10 minutes and benzyl chloroformate (33.8 mL, 229 mmol) is added keeping the internal temperature below 20° C. during the addition. The mixture is warmed to room temperature over 4 hours. The organic layer is separated, washed with brine, dried over sodium sulfate, and concentrated to dryness to give the title compound (54 g, 98%). ES/MS (m/e): 240 (M+H).

Preparation 3

Benzyl N-allyl-N-(2,2-dimethoxyethyl)carbamate

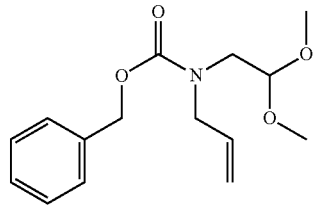 [SMILES: C=CCN(CC(OC)OC)C(=O)OCc1ccccc1]

A solution of benzyl N-(2,2-dimethoxyethyl)carbamate (50 g, 208.9 mmol) in toluene (180 mL) is treated with solid potassium hydroxide (51.6 g, 919.69 mmol) under nitrogen. After 10 minutes, benzyltriethylammonium chloride (0.8 g, 3.1 mmol) is added. After another 10 minutes a solution of allyl bromide (33 g, 272.8 mmol) in toluene (50 mL) is added drop wise over 10 minutes. The resultant mixture is stirred at 50° C. for 48 hours. The mixture is cooled to room temperature and quenched with water. The organic layer is separated, washed with brine, dried over magnesium sulfate, and concentrated to dryness to give the title compound (44 g, 75%). ES/MS (m/e): 280 (M+H).

Preparation 4

Benzyl N-allyl-N-(2-oxoethyl)carbamate

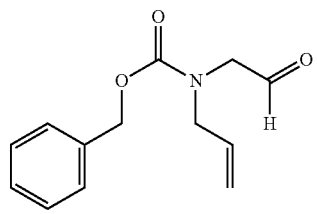 [SMILES: C=CCN(CC=O)C(=O)OCc1ccccc1]

A solution of benzyl N-allyl-N-(2,2-dimethoxyethyl)carbamate (30 g, 107 mmol) in formic acid (36.8 mL, 860 mmol) and water (4.84 mL) is stirred at room temperature overnight. The mixture is concentrated and diluted with hexanes/EtOAc (1:2) and water. The organic layer is separated, washed with brine solution until pH=6, and dried over sodium sulfate. The solvent is evaporated to give the title compound (25 g, 99%). ES/MS (m/e): 234 (M+H).

Preparation 5

1-(3-Bromophenyl)-2-(diallylamino)ethanone oxime

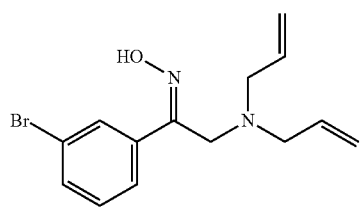 [SMILES: C=CCN(CC=C)C/C(=N/O)c1cccc(Br)c1]

A solution of 1-(3-bromophenyl)-2-(diallylamino)ethanone (60 g, 204.7 mmol) in ethanol (720 mL) and pyridine (24.8 mL, 307 mmol) is stirred 15 minutes at 22° C. Hydroxylamine hydrochloride (17 g, 246 mmol) is added in portions to the solution over 1 hour. The reaction is warmed to 50° C. for 2 hours and then heated to 70° C. for 16 hours. The solvent is evaporated and the residue partitioned in water (300 mL) and MTBE (300 mL). The organic layer is separated and washed with water (100 mL, 2×) and brine (100 mL). The organic layer is dried over sodium sulfate, filtered, and evaporated to dryness to give the title compound (75.5 g, 79%). ES/MS (m/e): 309 (M+1).

Preparation 6

2-(Diallylamino)-1-(2-fluorophenyl)ethanone oxime

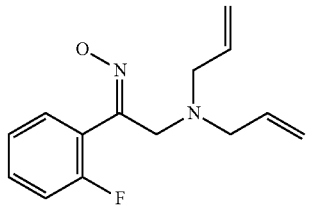 [SMILES: C=CCN(CC=C)C/C(=N/O)c1ccccc1F]

Diallyl amine (1.56 L, 12.2 mol) is added to a solution of 2-bromo-1-(2-fluorophenyl)ethanone (1291 g, 5.8 mol), in ethanol (12.9 L) keeping the internal temperature below 30° C. The reaction mixture is stirred for 4 hours at 22° C. Hydroxylamine hydrochloride (543 g, 7.58 mol) is added in portions to the solution and then heated for 16 hours at 70° C. The reaction is cooled to room temperature, the solvent is evaporated, and the residue is partitioned in water (5.1 L) and MTBE (6.4 L). Sodium carbonate is added to adjust the aqueous layer to pH=5.5 and the aqueous layer is extracted with additional MTBE (1.2 L). The organic layers are combined and washed with water and brine. The organic layer is dried over sodium sulfate, filtered, and evaporated to dryness to give the crude title compound (1.45 kg, 104%) which is used without further purification. ES/MS (m/e): 249 (M+1).

Preparation 7

Benzyl N-allyl-N-[2-hydroxyiminoethyl]carbamate

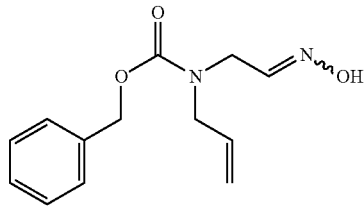 [SMILES: C=CCN(CC=NO)C(=O)OCc1ccccc1]

A solution of benzyl N-allyl-N-(2-oxoethyl)carbamate (25 g, 107 mmol) in acetonitrile (150 mL) is treated with hydroxylamine hydrochloride (9.68 g, 139 mmol) and a solution of sodium acetate trihydrate (16 g, 117.9 mmol) in water (75 mL). The mixture is stirred at room temperature overnight. The acetonitrile is evaporated and the aqueous solution is extracted with EtOAc. The organic layer is separated, dried over magnesium sulfate, and concentrated under vacuum to give the title compound (24 g, 90%). ES/MS (m/e): 249 (M+H).

Preparation 8

2-Bromo-1-(5-bromo-2-fluorophenyl)ethan-1-one

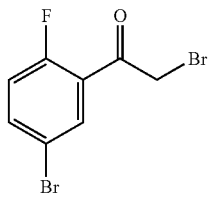 [SMILES: O=C(CBr)c1cc(Br)ccc1F]

N-bromosuccinimide (984 g, 5.53 mol) is added portionwise to a solution of 1-(5-bromo-2-fluorophenyl)ethan-1-one (1000 g, 4.6 mol) and p-toluene sulfonic acid (1315 g, 7.64 mol) in DCM (7 L) at 35° C. The mixture is stirred and heated to 40° C. The mixture is cooled to 24° C., and 7% NaHCO$_3$ (5 L) is added. The layers are separated and the organic layer is washed with 10% Na$_2$SO$_3$ (5 L) and water (5 L). The organic layer is concentrated to 2-3 volumes to give the title compound which is used without further purification.

Preparation 9

5-Allyl-6a-(5-bromo-2-fluorophenyl)-1-(4-methoxybenzyl)hexahydro-1H-pyrrolo[3,4-c]isoxazole

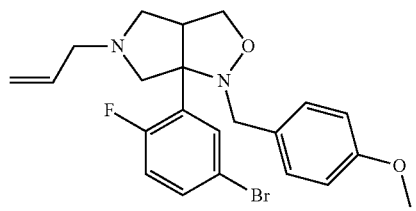 [SMILES: C=CCN1CC2CON(Cc3ccc(OC)cc3)C2(c2cc(Br)ccc2F)C1]

To a solution of 2-bromo-1-(5-bromo-2-fluorophenyl)ethan-1-one (1363 g, 4.61 mol) in toluene (10 L) is added diallylamine (537 g, 5.53 mol) and dipea (2381 g, 18.42 mol). The mixture is stirred for 4 hours at 40° C. to give 1-(5-bromo-2-fluorophenyl)-2-(diallylamino)ethan-1-one, which is not isolated. N-(4-methoxybenzyl)hydroxylamine (847 g, 5.53 mol) and Ti(OiPr)$_4$ (1965 g, 6.91 mol) are added to the mixture containing crude 1-(5-bromo-2-fluorophenyl)-2-(diallylamino)ethan-1-one. The mixture is stirred at 90° C. for 2 hours. The mixture is cooled to 20° C., and 50% citric acid monohydrate (4 L) and saturated Na$_2$CO$_3$ (4 L) are added. The layers are separated and the aqueous is extracted with MTBE (5 L). The organic extract is washed with water (5 L), and filtered through diatomaceous earth and concentrated to dryness. EtOAc (10 L) and Oxalic acid (580 g) are added to the residue and a solid is filtered and added to 1 N NaOH (13 L). MTBE (5 L) is added and the mixture is filtered through diatomaceous earth. The layers are separated and the organic layer is concentrated to 2 volumes. Heptane (3 L) is added and the solution is cooled to 10° C. The resulting solid is filtered to give the title compound (1330 g, 64%). ¹H NMR (400 MHz, CDCl₃) δ: 2.51-2.49 (m, 3H), 3.09-3.04 (m, 3H), 3.78-3.41 (m, 6H), 4.01 (m, 1H), 5.24-5.01 (m, 2H), 5.89-5.85 (m, 1H), 6.82-6.80 (m, 2H), 7.51-7.13 (m, 3H), 7.63-7.62 (m, 1H), 7.65-7.64 (m, 1H).

Preparation 10

5-Allyl-6a-(3-bromophenyl)-3,3a,4,6-tetrahydro-1H-pyrrolo[3,4-c]isoxazole

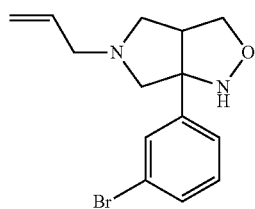 [SMILES: C=CCN1CC2CONC2(c2cccc(Br)c2)C1]

The crude 1-(3-bromophenyl)-2-(diallylamino)ethanone oxime (75.5 g, 195.34 mmol) is dissolved in toluene (600 mL) and refluxed for 12 hours. The solvent is evaporated in vacuo and the residue dissolved in a mixture of aqueous 1 N HCl (1 L) and MTBE (300 mL). The mixture is stirred for 15 minutes and diatomaceous earth (10 g) is added. The mixture is stirred for an additional 20 minutes and filtered through diatomaceous earth. The filter cake is washed with additional aqueous 1 N HCl (200 mL) and MTBE (200 mL). The organic layer is separated and washed with 1 N HCl (2×100 mL). The aqueous layers are combined and the pH adjusted to 9 with NaOH 50% w/w. The aqueous mixture is extracted with MTBE (3×250 mL). The organic layers are combined, dried over sodium sulfate, and filtered. The filtrate is evaporated and dried under vacuum to give a red solid (60 g). The red solid is diluted with heptane (600 mL) and the mixture heated to reflux for 20 minutes. Charcoal (2 g) is added and the mixture is filtered through diatomaceous earth. The filtrates are concentrated under atmospheric pressure to adjust the final volume to 300 mL. The solution is cooled to 22° C. and stirred for 3 hours. A pale yellow solid is collected by filtration and dried under vacuum to a constant weight to give the title compound (40 g, 60%). ES/MS (m/e): 309 (M+1).

Preparation 11

5-Allyl-6a-(2-fluorophenyl)-3,3a,4,6-tetrahydro-1H-pyrrolo[3,4-c]isoxazole

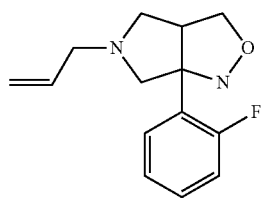 [SMILES: C=CCN1CC2CONC2(c2ccccc2F)C1]

Flow chemistry reaction step: A 343-ml seamless stainless steel tubular reactor (O.D=⅛ inch) is placed inside a GC oven and flushed with toluene at 20 mL/min for 20 minutes.

Apply back pressure of nitrogen (720 psig) and set the temperature of the GC to 210° C. After the temperature has reached 210° C., a solution of 2-(diallylamino)-1-(2-fluorophenyl)ethanone oxime (480.51 g, 1.74 mol) in toluene (5.81 L) is pumped through the reactor at 22.866 mL/min using a pair of high-pressure syringe pumps working in continuous mode to give a residence time of 15 minutes. After all the stock solution is consumed the reactor is flushed with toluene at 22.866 mL/min for 30 minutes. The temperature of the GC oven is set to 25° C. and the complete solution is collected and concentrated under vacuum. The solvent is evaporated and residue dissolved in methylene chloride (2.5 L) and water (5 L). The pH is adjusted to 1 with hydrochloric acid and the aqueous layer is separated and neutralized with sodium hydroxide to adjust the pH to 10. The aqueous layer is extracted with MTBE (3×2.5 L). The organic extracts are combined, dried over sodium sulfate, filtered, and evaporated to dryness to give the crude title compound (248 g, 47%) which is used without further purification. ES/MS (m/e): 249 (M+1).

Preparation 12

5-Allyl-6a-(5-bromo-2-fluorophenyl)hexahydro-1H-pyrrolo[3,4-c]isoxazole hydrochloride

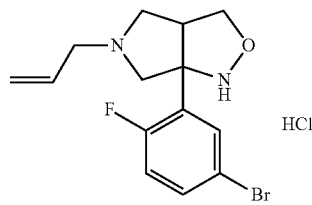 [SMILES: C=CCN1CC2CONC2(c2cc(Br)ccc2F)C1 ; Cl]

Trifluoroacetic acid (4 L, 52.9 mol) is added drop wise to a solution of 5-allyl-6a-(5-bromo-2-fluorophenyl)-1-(4-methoxybenzyl)hexahydro-1H-pyrrolo[3,4-c]isoxazole (1990 g, 4.45 mol) in DCM (12 L) at a rate to maintain the temperature below 35° C. After the addition is complete, the mixture is warmed to 33-43° C. and stirred for 6 hours. NaOH (20%, 10 L) is added at a rate to maintain the temperature below 35° C. The layers are separated and the organic layer is washed with water (6 L). The solution is concentrated, ethanol (16 L) is added, and the mixture is filtered through diatomaceous earth. The filtrate is concentrated and EtOAc (10 L) is added. 4 M HCl in EtOAc (8 L) is added and the resulting solid is filtered and dried to give the title compound (1385 g, 85.6%). ES m/z 327.1 (M+1)

Preparation 13

Benzyl 3,3a,4,6-tetrahydropyrrolo[3,4-c]isoxazole-5-carboxylate

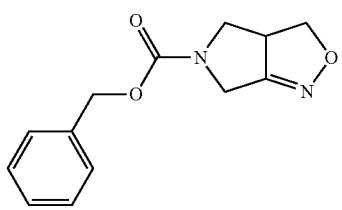 [SMILES: O=C(OCc1ccccc1)N1CC2=NOCC2C1]

A solution of benzyl N-allyl-N-[2-hydroxyiminoethyl] carbamate (24 g, 96.6 mmol) in DCM (338 mL) is treated drop wise over 10 minutes with a 5% w/w aqueous solution of sodium hypochlorite (106.08 mmol, 143.06 mL). The resultant mixture is stirred at room temperature overnight. The reaction is quenched with a 40% aqueous solution of sodium bisulfite (7 g). The organic layer is separated, dried over magnesium sulfate, and concentrated under vacuum. The crude product is purified over silica gel eluting with 5% EtOAc in hexanes to give the title compound (18 g, 75%). ES/MS (m/e): 247 (M+H).

Preparation 14

Benzyl 6a-(5-bromo-2-fluoro-phenyl)-3,3a,4,6-tetrahydro-1H-pyrrolo[3,4-c]isoxazole-5-carboxylate

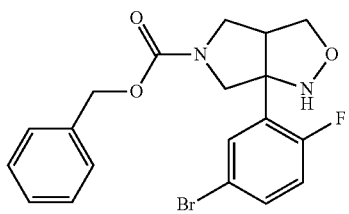 [SMILES: O=C(OCc1ccccc1)N1CC2CONC2(c2cc(Br)ccc2F)C1]

A 1.6 M hexanes solution of n-butyl lithium (25.4 mL, 40.6 mmol) is added drop wise to a −78° C. solution of 4-bromo-1-fluoro-2-iodobenzene (12.22 g, 40.6 mmol) in THF (60 mL) to give a yellow solution that is stirred at −78° C. for 15 minutes. Boron trifluoride etherate (5.14 mL, 40.6 mmol) is added to a separate −78° C. solution of benzyl 3,3a,4,6-tetrahydropyrrolo[3,4-c]isoxazole-5-carboxylate (5 g, 20.3 mmol) in THF (60 mL) and the mixture is stirred at −78° C. for 5 minutes. This solution is added to the previously prepared −78° C. organolithium mixture via cannula. The combined mixture is stirred for 30 minutes at −78° C. The mixture is quenched with saturated aqueous ammonium chloride and warmed to room temperature. The mixture is extracted with EtOAc (3×) and the organic extracts are combined, dried over sodium sulfate, filtered and the solvent removed in vacuo. The crude product is purified over silica gel with a 35 minute 5% to 100% EtOAc in hexanes gradient to give the title compound (2.27 g, 27%). ES/MS (m/e): ($^{79}$Br/$^{81}$Br) 421/423 (M+H).

Preparation 15

Benzyl 1-(benzoylcarbamothioyl)-6a-(5-bromo-2-fluoro-phenyl)-3,3a,4,6-tetrahydropyrrolo[3,4-c]isoxazole-5-carboxylate

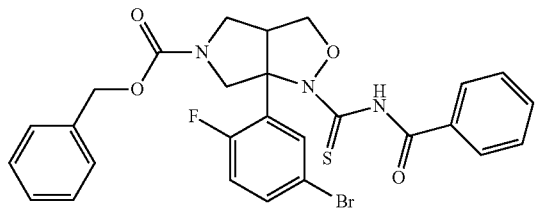 [SMILES: O=C(NC(=S)N1OCC2CN(C(=O)OCc3ccccc3)CC21c1cc(Br)ccc1F)c1ccccc1]

Benzoyl isothiocyanate (2.87 mL, 21.28 mmol) is added drop wise to a solution of benzyl 6a-(5-bromo-2-fluorophenyl)-3,3a,4,6-tetrahydro-1H-pyrrolo[3,4-c]isoxazole-5-carboxylate (5.977 g, 14.2 mmol) in THF (95 mL) and stirred overnight under nitrogen. The solvent is removed in vacuo. The crude product is purified over silica gel with a 30 minute 5% to 100% EtOAc in hexanes gradient to give the title compound (6.05 g, 73%). ES/MS (m/e): ($^{79}$Br/$^{81}$Br) 584/586 (M+H).

Preparation 16

Benzyl 3-(benzoylcarbamothioylamino)-3-(5-bromo-2-fluoro-phenyl)-4-(hydroxymethyl)pyrrolidine-1-carboxylate

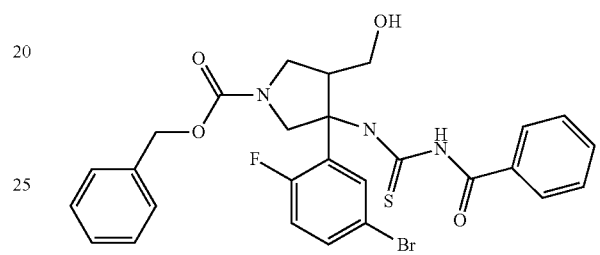

A mixture of benzyl 1-(benzoylcarbamothioyl)-6a-(5-bromo-2-fluoro-phenyl)-3,3a,4,6-tetrahydropyrrolo[3,4-c]isoxazole-5-carboxylate (6.05 g 10.4 mmol) and zinc (dust, <10 micron) (6.77 g, 103.5 mmol) is stirred in acetic acid (52 mL) at room temperature overnight under nitrogen. The reaction is diluted with EtOAc and filtered through diatomaceous earth. The solvent is removed in vacuo and the residue is diluted with EtOAc, water, and saturated aqueous sodium bicarbonate. The mixture is extracted with EtOAc (3×), the combined organic layers are combined and dried over sodium sulfate, filtered, and the solvent removed in vacuo. The crude product is purified over silica gel with a 30 minute 5% to 100% EtOAc in hexanes gradient to give the title compound (5.222 g, 86%). ES/MS (m/e): ($^{79}$Br/$^{81}$Br) 586/588 (M+H).

Preparation 17

(1-Allyl-4-amino-4-(5-bromo-2-fluorophenyl)pyrrolidin-3-yl)methanol

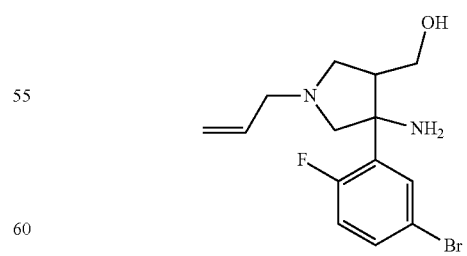

A saturated aqueous solution of sodium carbonate is added to a solution of 5-allyl-6a-(5-bromo-2-fluorophenyl) hexahydro-1H-pyrrolo[3,4-c]isoxazole hydrochloride (1400 g, 3.85 mol) in DCM (7 L) to reach a pH>9. The layers are separated and the organic extract concentrated to 1.5 volumes. Acetic acid (1.38 L) is added the solution concentrated to 2 L. Acetic acid (7 L) and zinc powder (2.5 kg, 38.5 mol) are added and the mixture is heated to 40-50° C. and stirred for 3 hours. EtOAc (9.8 L) is added and the mixture is filtered through diatomaceous earth. The filter cake is washed with EtOAc (4 L). The filtrate is separated and water (7 L) is added to the combined organics. Ammonium hydroxide is added to reach a pH ≥9. The layers are separated and the organic layer is concentrated to 2 L. Ethanol (2.8 L) is added and the solution is concentrated to 2 L. Ethanol (19 L) is added and the mixture is filtered through diatomaceous earth to give an ethanol solution of the title compound, which is used without further purification.

Preparation 18

[1-Allyl-4-amino-4-(3-bromophenyl)pyrrolidin-3-yl]methanol

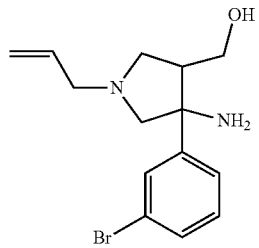 [SMILES: C=CCN1CC(CO)C(N)(c2cccc(Br)c2)C1]

A 22° C. solution of 5-allyl-6a-(3-bromophenyl)-3,3a,4,6-tetrahydro-1H-pyrrolo[3,4-c]isoxazole (40 g, 129.4 mmol) in acetic acid (400 mL) is treated with zinc dust (42.3 g, 646.8 mmol) in one portion. The reaction is stirred vigorously at room temperature for 1 hour. EtOAc (400 mL) is added and the mixture is filtered through diatomaceous earth. The filtrate is evaporated and the residue dried under vacuum. The residue is partitioned in water (300 mL) and MTBE (300 mL). The pH is adjusted to 8 with sodium hydroxide 50% w/w and the organic layer is separated, dried over sodium sulfate, and filtered. The filtrate is evaporated and the residue is dried under vacuum to give the title compound (41 g, 97%). ES/MS (m/e): 311 (M+1).

Preparation 19

1-Allyl-4-amino-4-(2-fluorophenyl)pyrrolidin-3-yl]methanol

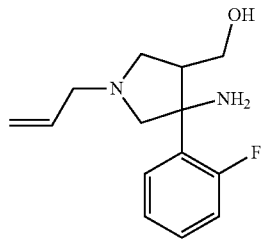 [SMILES: C=CCN1CC(CO)C(N)(c2ccccc2F)C1]

Zinc dust (590 g, 9 mol) is added to a solution of 5-allyl-6a-(2-fluorophenyl)-3,3a,4,6-tetrahydro-1H-pyrrolo[3,4-c]isoxazole (3559 g, 1.29 mol) in a mixture of methanol (2.85 L) and ammonium chloride saturated aqueous solution (3.56 L) and mixture is heated for 16 hours at 70° C. The reaction is cooled to 60° C., diluted with THF (2.85 L), and filtered while hot over diatomaceous earth. The filtrate is evaporated to remove the organic solvent, and the aqueous mixture is diluted with citric acid 10% w/w aqueous solution (4 L) and EtOAc (3.5 L). The organic layer is separated and the aqueous layer washed with EtOAc (2×2 L). The aqueous layer is neutralized with sodium hydroxide 50% w/w to adjust the pH to 10, and then is extracted with EtOAc (2×1.5 L). The organic extracts are combined, dried over sodium sulfate, filtered, and evaporated to dryness to give the crude title compound (299 g, 92%). ES/MS (m/e): 251 (M+1).

Preparation 20

[(3S,4R)-1-allyl-3-(5-bromo-2-fluoro-phenyl)-4-(hydroxymethyl)pyrrolidin-3-yl]ammonium;(2S,3S)-4-hydroxy-2,3-bis[(4-methylbenzoy)oxy]-4-oxo-butanoate

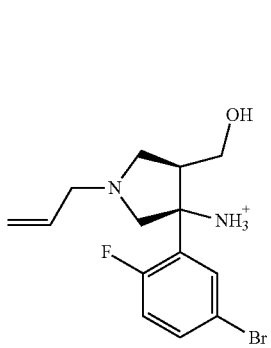 [SMILES: C=CCN1C[C@@H](CO)[C@](N)(c2cc(Br)ccc2F)C1]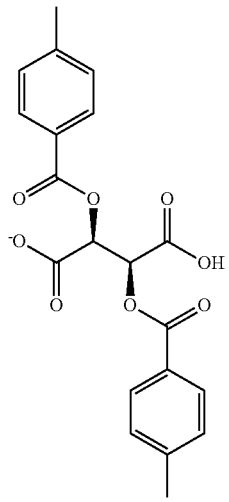

Di-p-toluoyl-L-tartaric acid monohydrate (1.04 kg, 2.69 mol) is added to a solution of (1-allyl-4-amino-4-(5-bromo-2-fluorophenyl)pyrrolidin-3-yl)methanol (1264 g. 3.85 mmol) in ethanol (21 L). The mixture is heated to 65-75° C. and stirred for 3 hours. The mixture is cooled to 5-10° C., a seed crystal is added of [(3S,4R)-1-allyl-3-(5-bromo-2-fluoro-phenyl)-4-(hydroxymethyl)pyrrolidin-3-yl]ammonium;(2S,3S)-4-hydroxy-2,3-bis[(4-methylbenzoy)oxy]-4-oxo-butanoate (1.0 g), and the mixture is stirred for 3 hours. The solid is filtered and the filter cake is washed with cold ethanol (1.4 L). The filter cake is dried to give the title compound as a white solid. Chiral analysis of the second eluting isomer: Column: IC Chiralpak, 4.6 mm*250 mm*5 μm; eluent: 90% hexane (0.3% diethylamine): 10% ethanol (0.3% diethylamine); flow rate of 1.0 mL/min at UV 270 nm confirms the enantiomerically enriched (99% ee) enantiomer with $R_t$=7.4 minutes, (1050 g, 38%). $^1$H NMR (400 MHz, CD$_3$OD) δ: 2.40 (s, 6H), 3.05-3.04 (m, 1H), 3.57-3.31 (m, 3H), 3.66-3.58 (m, 4H), 3.75-3.74 (m, 2H), 5.38-5.36 (m, 1H), 5.50-5.46 (m, 1H), 5.88 (s, 2H), 5.97-5.91 (m, 1H), 7.10-7.05 (m, 1H), 7.29 (d, J=8.0 Hz, 4H), 7.53-7.51 (m, 1H), 7.80-7.78 (m, 1H), 8.01 (d, J=8.0 Hz, 4H).

Preparation 21

[(3R,4S)-1-Allyl-4-amino-4-(2-fluorophenyl)pyrrolidin-3-yl]methanol; 2,3-bis[(4-methylbenzoy)oxy]butanedioic acid

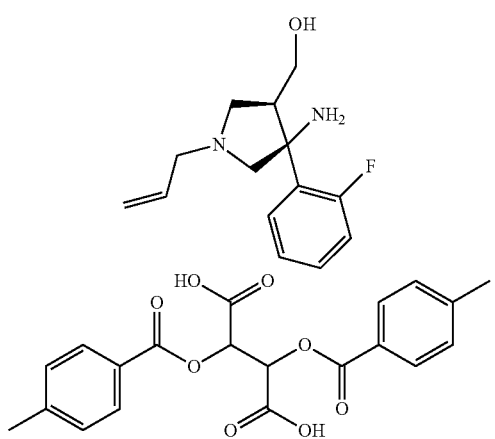

A solution of di-p-toluoyl-L-tartaric acid (348.6 g, 884 mmol) in 1-methoxy-2-propanol (1.13 L) is added to a solution of [(3R,4S)-1-allyl-4-amino-4-(2-fluorophenyl)pyrrolidin-3-yl]methanol (225.9 g, 902 mmol), in 1-methoxy-2-propanol (1.13 L) previously heated at 40° C. The reaction is cooled to 22° C. and stirred for 18 hours. A white solid is collected by filtration and washed with 1-methoxy-2-propanol (600 ml). The collected solid is dried to give the title compound (183.01 g, 31.8%). ES/MS (m/e): 251 (M+1).

Preparation 22

[(3R,4S)-1-Allyl-4-amino-4-(3-bromophenyl)pyrrolidin-3-yl]methanol; (2R,3R)-2,3-bis[(4-methylbenzoy)oxy]butanedioic acid

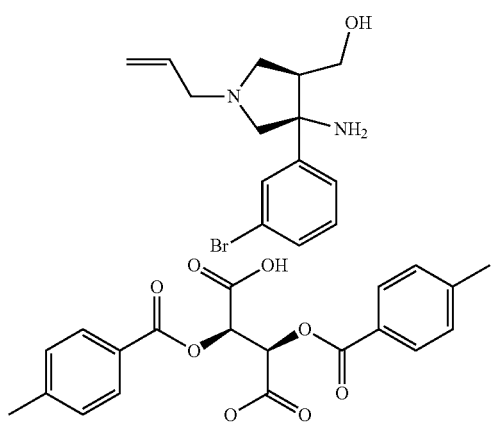

A solution of [1-allyl-4-amino-4-(3-bromophenyl)pyrrolidin-3-yl]methanol (77 g, 235 mmol) in isopropyl alcohol (914 mL) is heated to 70° C. Di-p-toluoyl-L-tartaric acid (86.2 g, 223 mmol) is added and the mixture is cooled to 22° C. for 2 hours and stirred overnight. The slurry is filtered to collect a pale yellow solid and washed with isopropyl alcohol. The solid is dried under vacuum to give the title compound (63 g, 36%). ES/MS (m/e): 311 (M+1). The product is analyzed by reverse phase chiral chromatography: Analysis of the first eluting isomer (Column: Chiralpak ID-3 4.6×50 mm; eluent: 70:30, aqueous 20 mM ammonium bicarbonate: acetonitrile; flow: 1.5 mL/min at UV 215 nm) confirms the enantiomerically enriched (96% ee) enantiomer with $R_t$=1.26 minutes.

Preparation 23

((3R,4 S)-1-Allyl-4-amino-4-(5-bromo-2-fluorophenyl)pyrrolidin-3-yl)methanol

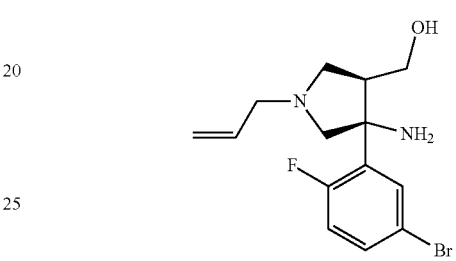

1 N HCl (500 mL, 500 mmol) is added to a 0° C. solution of [(3S,4R)-1-allyl-3-(5-bromo-2-fluoro-phenyl)-4-(hydroxymethyl)pyrrolidin-3-yl]ammonium;(2S,3S)-4-hydroxy-2,3-bis[(4-methylbenzoy)oxy]-4-oxo-butanoate (100 g, 139.4 mmol) in EtOAc (500 mL). The mixture is stirred for 1 hour. The aqueous layer is separated and the pH is adjusted to 8 with 1 N NaOH. The aqueous layer is extracted with EtOAc (350 mL×2). The organic layers are combined, washed with water (500 mL) and concentrated to give the title compound (40 g, 87%). Chiral analysis of the second eluting isomer: Column: IC Chiralpak, 4.6 mm*250 mm*5 μm; eluent: 90% hexane (0.3% diethylamine):10% ethanol (0.3% diethylamine); flow rate of 1.0 mL/min at UV 270 nm confirms the enantiomerically enriched (99.7% ee) enantiomer with $R_t$=7.4 minutes. $^1$H NMR (400 MHz, CDCl$_3$ δ: 2.78-2.70 (m, 5H), 3.16-3.00 (m, 3H), 3.87-3.75 (m, 1H), 3.90-3.84 (m, 1H), 5.24-5.11 (m, 2H), 5.91-5.87 (m, 1H), 6.95-6.91 (m, 1H), 7.35-7.32 (m, 1H), 7.67-7.65 (m, 1H).

Preparation 24

[(3R,4S)-1-Allyl-4-amino-4-(2-fluorophenyl)pyrrolidin-3-yl]methanol

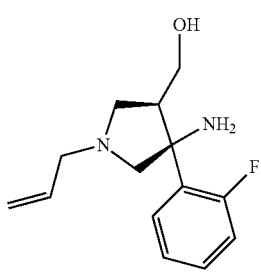 [SMILES: C=CCN1C[C@@H](CO)[C@](N)(c2ccccc2F)C1]

[(3R,4S)-1-Allyl-4-amino-4-(2-fluorophenyl)pyrrolidin-3-yl]methanol;2,3-bis[(4-methylbenzoy)oxy]butanedioic acid (211 g, 331 mmol) is dissolved in water (2.1 L) and EtOAc (2.3 L). Hydrochloric acid 35% w/w is added to adjust the pH to 1. The aqueous layer is separated and the pH adjusted to 10 with sodium hydroxide 50% w/w and extracted with EtOAc (2×). The pH of the aqueous layer is adjusted to 10 with aqueous NaOH, and extracted with MTBE (3×) while also maintaining the pH of the aqueous solution at pH=10. The organic extracts are combined, dried over sodium sulfate, filtered, and concentrated to dryness to give the crude title compound, (73 g, 88%, 94.8% ee). The product is analyzed by chiral chromatography: Column AS-H, eluent 10% isopropyl alcohol, 2% isopropyl amine; flow rate of 3 mL/min at UV 220; pressure of 100 bar at 35° C. to give the title compound as the second eluting isomer, R$_f$=2.26 minutes. ES/MS (m/e): 251 (M+1).

Preparation 25

N-(((3S,4R)-1-Allyl-3-(5-bromo-2-fluorophenyl)-4-(hydroxymethyl)pyrrolidin-3-yl)carbamothioyl)benzamide

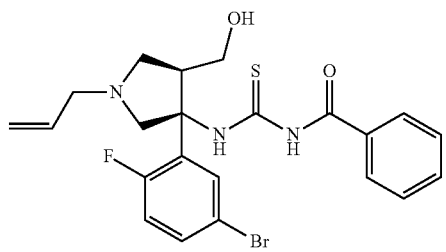 [SMILES: C=CCN1C[C@@H](CO)[C@](NC(=S)NC(=O)c2ccccc2)(c2cc(Br)ccc2F)C1]

Benzoyl isothiocyanate (15.0 g, 91.9 mmol) is added to a 0° C. solution of ((3R,4S)-1-allyl-4-amino-4-(5-bromo-2-fluorophenyl)pyrrolidin-3-yl)methanol (30 g, 91.1 mmol) in THF (400 mL). The solution is warmed to 25° C. and stirred for 1 hour to give a THF solution of the title compound, which is used without further purification.

Preparation 26

[(3R,4S)-1-Allyl-4-amino-4-(3-bromophenyl)pyrrolidin-3-yl]methanol

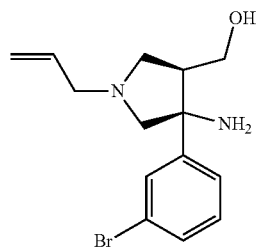 [SMILES: C=CCN1C[C@@H](CO)[C@](N)(c2cccc(Br)c2)C1]

[(3R,4S)-1-Allyl-4-amino-4-(3-bromophenyl)pyrrolidin-3-yl]methanol; (2R,3R)-2,3-bis[(4-methylbenzoyl)oxy]butanedioic acid (63 g 85.8 mmol) is combined with aqueous 1 N HCl (800 mL) and EtOAc (400 mL) and the mixture is stirred for 15 minutes at 22° C. The layers are separated and the pH of the aqueous layer is adjusted to 10 with sodium hydroxide 50% w/w. The aqueous mixture is extracted with MTBE (3×250 mL). The combined organic layers are dried over magnesium sulfate, filtered, and evaporated to dryness to give the title compound (27 g, 99%). ES/MS (m/e): 311 (M+1).

Preparation 27

N-[(4aR,7aS)-6-Allyl-7a-(3-bromophenyl)-4,4a,5,7-tetrahydropyrrolo[3,4-d][1,3]thiazin-2-yl]benzamide

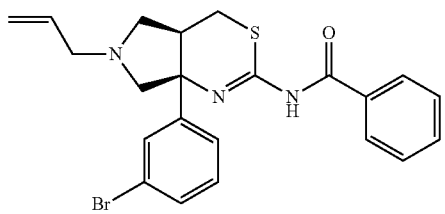 [SMILES: C=CCN1C[C@H]2CSC(NC(=O)c3ccccc3)=N[C@@]2(c2cccc(Br)c2)C1]

A solution of [(3R,4S)-1-allyl-4-amino-4-(3-bromophenyl)pyrrolidin-3-yl]methanol (27 g; 86.7 mmol) in THF (270 mL) is cooled to −5° C. under a nitrogen atmosphere. Benzoyl isothiocyanate (12.3 mL, 91 mmol) is added drop wise keeping the temperature below 0° C. The reaction is allowed to warm to 22° C. for 1 hour. 1,1'-Carbonyldiimidazole (28.1 g, 173.5 mmol) is added in a single portion and the reaction is stirred for 1 hour at 22° C. and then heated to reflux for 16 hours. The solvent is removed in vacuo and the residue is dried under vacuum. The crude material is partitioned in MTBE (500 mL) and water (250 mL). The organic layer is separated, dried over magnesium sulfate, filtered, and evaporated to dryness. The crude material is purified over a silica gel gradient of 90/10 to 60/40 DCM/EtOAc to give the title compound (27 g, 68%). ES/MS (m/e): 456 (M+1).

Preparation 28

N-((4aR,7aS)-6-Allyl-7a-(5-bromo-2-fluorophenyl)-4,4a,5,6,7,7a-hexahydropyrrolo[3,4-d][1,3]thiazin-2-yl)benzamide, dihydrochloride

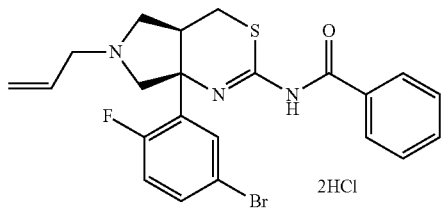 [SMILES: C=CCN1C[C@H]2CSC(NC(=O)c3ccccc3)=N[C@@]2(c2cc(Br)ccc2F)C1]

Triphenylphosphine (36.8 g, 140.3 mmol) is added to a THF (400 mL) solution of N-(((3S,4R)-1-allyl-3-(5-bromo-2-fluorophenyl)-4-(hydroxymethyl)pyrrolidin-3-yl)carbamothioyl)benzamide (91.1 mmol). Di-t-butyl azodicarboxylate (31.6 g, 137.2 mmol) in THF (100 mL) is added.

The mixture is stirred at 20-30° C. for 2 hours. The mixture is concentrated and MTBE (400 mL) is added. The solution is filtered through diatomaceous earth and the cake is washed with MTBE (130 mL). The filtrates are combined and 1 N HCl in EtOAc (200 mL) is added. The mixture is stirred for 2 hours and then concentrated to 500 mL. MTBE (320 mL) is added and the solution is filtered and washed with heptane (130 mL). The solid is slurried in EtOAc (650 mL) and stirred at 50-60° C. for 2 hours The hot slurry is filtered and the solid is washed with EtOAc (130 mL) and heptane (130 mL). The solid is reslurried in EtOAc (650 mL) and stirred for 2 hours at 50-60° C. The hot slurry is filtered and washed with EtOAc (130 mL) and heptane (130 mL). The solid is dried to give the title compound as the di-HCl salt (40 g, 80%, 99.5% ee). Chiral analysis of the first eluting isomer: Column: IC Chiralpak, 4.6 mm*250 mm*5 μm; eluent: 85% hexane (0.1% diethylamine): 15% isopropyl alcohol (0.1% diethylamine); flow rate of 1.0 mL/min at UV 282 nm confirms the enantiomerically enriched (99.5% ee) enantiomer with $R_f$=12.5 minutes.

Preparation 29

N-((4aR,7aS)-6-Allyl-7a-(2-fluoro-5-(2,2,2-trifluoroacetamido)phenyl)-4,4a,5,6,7,7a-hexahydropyrrolo[3,4-d][1,3]thiazin-2-yl)benzamide

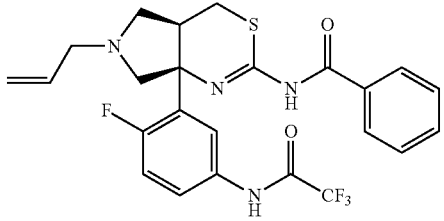 [SMILES: C=CCN1C[C@H]2CSC(NC(=O)c3ccccc3)=N[C@@]2(c2cc(NC(=O)C(F)(F)F)ccc2F)C1]

15% Sodium carbonate (440 mL) is added to a solution of N-((4aR,7aS)-6-allyl-7a-(5-bromo-2-fluorophenyl)-4,4a,5,6,7,7a-hexahydropyrrolo[3,4-d][1,3]thiazin-2-yl)benzamide dihydrochloride (495 g, 717.88 mmol) in EtOAc (3 L) and water (784 mL). The mixture is stirred for 1-2 hours. The layers are separated and the organic layer is filtered through silica gel (40 g) and washed with EtOAc (600 mL). The filtrate is concentrated to dryness to give N-((4aR,7aS)-6-allyl-7a-(5-bromo-2-fluorophenyl)-4,4a,5,6,7,7a-hexahydropyrrolo[3,4-d][1,3]thiazin-2-yl)benzamide. Trifluoroacetamide (136.7 g, 1.21 mol), NaI (182.5 g, 1.22 mol), 4 A molecular sieves (342 g), and $K_2CO_3$ (170.9 g, 1.24 mol) are added to a solution of N-((4aR,7aS)-6-allyl-7a-(5-bromo-2-fluorophenyl)-4,4a,5,6,7,7a-hexahydropyrrolo[3,4-d][1,3]thiazin-2-yl)benzamide (341 g, 494.54 mmol) in DMSO (525 mL) and 1,4-dioxane (1.025 L). Trans-N,N'-dimethylcyclohexane (81.6 g, 573.66 mmol) and copper iodide (27.3 g, 143.34 mmol) in DMSO (500 mL) are added to the reaction mixture. The mixture is stirred for 5 minutes. The mixture is warmed to 100° C. and stirred for 8 hours and cooled to 24° C. Water (5.9 L) and DCM (5.9 l) are added, the mixture is filtered, and the layers are separated. The organic layer is washed with water (5.9 L) to obtain the title compound in a solution of DCM, which is used without further purification.

Preparation 30

N-((4aR,7aS)-6-Allyl-7a-(5-amino-2-fluorophenyl)-4,4a,5,6,7,7a-hexahydropyrrolo[3,4-d][1,3]thiazin-2-yl)benzamide, hydrochloride

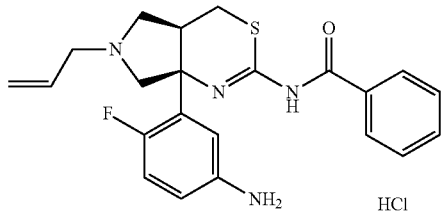 [SMILES: C=CCN1C[C@H]2CSC(NC(=O)c3ccccc3)=N[C@@]2(c2cc(N)ccc2F)C1 ; Cl]

Sodium hydroxide (28.7 g) and water (2.7 L) are added to a DCM solution of N-((4aR,7aS)-6-allyl-7a-(2-fluoro-5-(2,2,2-trifluoroacetamido)phenyl)-4,4a,5,6,7,7a-hexahydropyrrolo[3,4-d][1,3]thiazin-2-yl)benzamide (250 g, 494.4 mmol) and the mixture is stirred at 24° C. for 68 hours. 1 N HCl (3.5 L) is added to obtain a pH of 1-3. The layers are separated and the aqueous layer is washed with DCM (680 mL). DCM (4 L) is added to the aqueous followed by 21% ammonium hydroxide to obtain a pH of 8-10. The layers are separated and organic extracts are combined, filtered through silica gel (170 g) and washed with DCM (1.4 L). The solvent is concentrated to dryness and diluted with EtOAc (4 L). 1 N HCl in EtOAc (700 mL) is added at a temperature below 25° C. and the mixture is stirred for 1 hour. The mixture is concentrated to about 7-8 volumes and EtOAc (2.8 L) is added. The resulting precipitate is filtered and washed with EtOAc (400 mL). The solid is dried to give the title compound. (246 g, 52%).

Preparation 31

N-((4aR,7aS)-7a-(5-Acetamido-2-fluorophenyl)-6-allyl-4,4a,5,6,7,7a-hexahydropyrrolo[3,4-d][1,3]thiazin-2-yl)benzamide

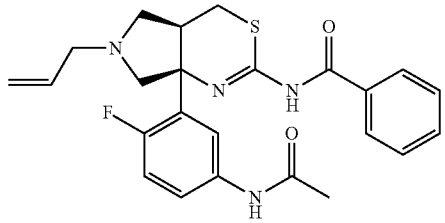 [SMILES: C=CCN1C[C@H]2CSC(NC(=O)c3ccccc3)=N[C@@]2(c2cc(NC(C)=O)ccc2F)C1]

Acetic anhydride (23.5 g, 0.23 mol) is added to a solution of N-((4aR,7aS)-6-allyl-7a-(5-amino-2-fluorophenyl)-4,4a,5,6,7,7a-hexahydropyrrolo[3,4-d][1,3]thiazin-2-yl)benzamide hydrochloride (100 g, 0.153 mol) and triethylamine (54.3 g, 0.535 mol) in DCM (800 mL). After stirring for 1 hour at 20-25° C., saturated $NaHCO_3$ (700 mL) and water (600 mL) are added. The layers are separated to give the title compound, which is used without further purification as a solution in DCM.

Preparation 32

N-[(4aR,7aS)-6-Allyl-7a-(2-fluorophenyl)-4,4a,5,7-tetrahydropyrrolo[3,4-d][1,3]thiazin-2-yl]benzamide

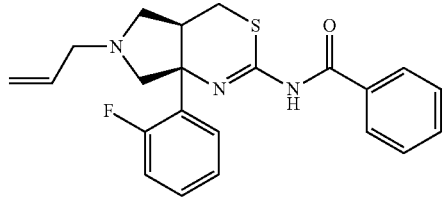 [SMILES: C=CCN1C[C@H]2CSC(NC(=O)c3ccccc3)=N[C@@]2(c2ccccc2F)C1]

A solution of [(3R,4S)-1-allyl-4-amino-4-(2-fluorophenyl)pyrrolidin-3-yl]methanol (129.7 g, 414 mmol) in THF (2.3 L) is cooled at 0° C. under a nitrogen atmosphere. Benzoyl isothiocyanate (61.5 mL, 456 mmol) is added keeping the temperature below 5° C. The reaction is warmed to room temperature over 3 hours and 1,1'-carbonyldiimidazole (87.4 g, 538.9 mmol) is added and the reaction stirred at 22° C. for 1 hour followed by heating at 70° C. for 16 hours. The reaction mixture is cooled to 22° C. and the solvent is evaporated. The residue is partitioned in EtOAc (1 L) and water (1 L). The organic layer is separated and the aqueous layer is extracted with EtOAc (2×400 mL). The organics are combined, dried over sodium sulfate, filtered, and evaporated to dryness to give the crude title compound. The crude product is purified by silica gel chromatography eluting with a gradient of EtOAc/DCM from 0-40% DCM to give the title compound as pale yellow solid (170 g, 99%) containing residual solvent. ES/MS (m/e): 396 (M+1).

Preparation 33

Benzyl 2-benzamido-7a-(5-bromo-2-fluoro-phenyl)-4,4a,5,7-tetrahydropyrrolo[3,4-d][1,3]thiazine-6-carboxylate

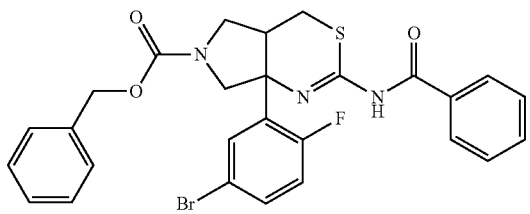 [SMILES: O=C(NC1=NC2(c3cc(Br)ccc3F)CN(C(=O)OCc3ccccc3)CC2CS1)c1ccccc1]

1,1'-carbonyldiimidazole (2.87 g, 17.7 mmol) is added to a solution of benzyl 3-(benzoylcarbamothioylamino)-3-(5-bromo-2-fluoro-phenyl)-4-(hydroxymethyl)pyrrolidine-1-carboxylate (5.198 g, 8.86 mmol) in THF (52 mL). The mixture is stirred for 1.5 hours at room temperature and then the reaction is heated at reflux overnight under nitrogen. The reaction is cooled, diluted with water, and extracted with EtOAc (3×). The organic layers are combined, dried over sodium sulfate, filtered, and the solvent removed in vacuo. The crude product is purified over silica gel with a 30 minute 5% to 100% EtOAc in hexanes gradient to give the title compound (2.93 g, 58%). ES/MS (m/e): ($^{79}$Br/$^{81}$Br). 568/570 (M+H)

Preparation 34

N-((4aR,7aS)-7a-(5-Acetamido-2-fluorophenyl)-4,4a,5,6,7,7a-hexahydropyrrolo[3,4-d][1,3]thiazin-2-yl)benzamide

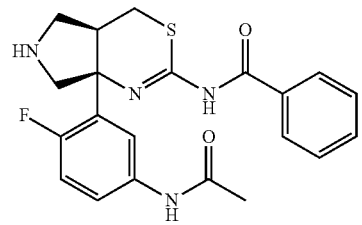 [SMILES: CC(=O)Nc1ccc(F)c([C@]23CNC[C@H]2CSC(NC(=O)c2ccccc2)=N3)c1]

Triphenylphosphine (4.0 g, 0.015 mol) and 1,3-dimethylbarbituric acid (15.2 g, 0.097 mol) are added to a DCM solution of N-((4aR,7aS)-7a-(5-acetamido-2-fluorophenyl)-6-allyl-4,4a,5,6,7,7a-hexahydropyrrolo[3,4-d][1,3]thiazin-2-yl)benzamide (0.153 mol). Palladium acetate (1.7 g, 7.7 mmol) is added and the mixture is stirred at 20 to 30° C. for 1 hour. 25% Ammonium hydroxide is added and the layers are separated. The organic layer is washed with HOAc (3.0 equiv in 500 mL of water) and the pH is adjusted to 8-9 with 25% ammonium hydroxide. The aqueous layer is extracted with DCM (2×500 mL). The organic extracts are combined and concentrated to 3-4 volumes. MTBE (1 L) is added and the mixture is filtered. The mixture is concentrated and heptane (1 L) is added. The resulting solid is filtered, collected, and dried to give the title compound (48 g, 76%). $^1$H NMR (400 MHz, CDCl$_3$) δ: 2.15 (s, 3H), 2.87-2.83 (m, 1H), 3.43-3.23 (m, 5H), 3.70-3.67 (m, 1H), 7.12-7.07 (m, 1H), 7.28-7.27 (m, 1H), 7.52-7.41 (m, 4H), 7.79 (m, 1H), 8.18-8.16 (m, 2H). ES m/z 413.1 (M+1).

Preparation 35

N-[(4aR,7aS)-7a-(3-Bromophenyl)-4a,5,6,7-tetrahydro-4H-pyrrolo[3,4-d][1,3]thiazin-2-yl]benzamide

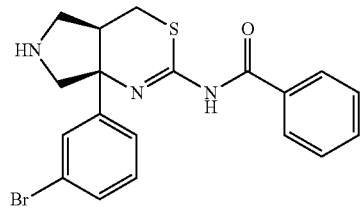 [SMILES: O=C(NC1=N[C@@]2(c3cccc(Br)c3)CNC[C@H]2CS1)c1ccccc1]

A room temperature mixture of N-[(4aR,7aS)-6-allyl-7a-(3-bromophenyl)-4,4a,5,7-tetrahydropyrrolo[3,4-d][1,3]thiazin-2-yl]benzamide (1 g, 2.19 mmol) and N,N-dimethylbarbituric acid (0.868 g, 5.48 mmol) in chloroform (22 mL) is degassed by bubbling nitrogen through the resulting slurry at room temperature for 5 minutes. The mixture is treated with tetrakis(triphenylphosphine)palladium (0.261 g, 219 μmol) and is stirred for 1.5 hours under nitrogen. In a separate flask, a mixture of N-[(4aR,7aS)-6-allyl-7a-(3-bromophenyl)-4,4a,5,7-tetrahydropyrrolo[3,4-d][1,3]thiazin-2-yl]benzamide (22.2 g, 48.6 mmol) and N,N-dimethylbarbituric acid (19.28 g, 121.6 mmol) in chloroform (486 mL) is degassed by bubbling nitrogen through the resulting slurry at room temperature for 5 min. The mixture is treated with tetrakis(triphenylphosphine)palladium (5.79 g, 4.86 mmol) and is stirred for 2 hours under nitrogen. The two reactions are combined and the solvent is removed in vacuo to give the crude product. The crude material is purified over silica gel with a 30 minute 0.5% to 10% methanol in DCM gradient to give the title compound (22.4 g, 100%). ES/MS (m/e): ($^{79}$Br/$^{81}$Br) 416/418 (M+H).

Preparation 36

N-[(4aR,7aS)-7a-(2-Fluorophenyl)-4a,5,6,7-tetrahydro-4H-pyrrolo[3,4-d][1,3]thiazin-2-yl]benzamide

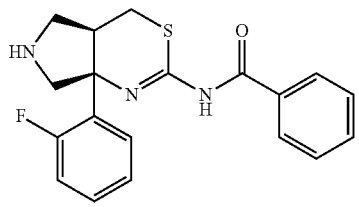 [SMILES: O=C(NC1=N[C@@]2(c3ccccc3F)CNC[C@H]2CS1)c1ccccc1]

Benzoic Acid, 2-mercapto-(122 g, 793 mmol), bis(dibenzylideneacetone)palladium (4.15 g, 7.21 mmol), and 1,4-bis(diphenylphosphino)butane (3.14 g, 7.21 mmol) are added to a solution of N-[(4aR,7aS)-6-allyl-7a-(2-fluorophenyl)-4,4a,5,7-tetrahydropyrrolo[3,4-d][1,3]thiazin-2-yl]benzamide (178.21 g, 360 mmol) in anhydrous 2-methyltetrahydrofuran (1.96 L) under a nitrogen atmosphere. The solution is degassed by vacuum/nitrogen cycles three times, and then nitrogen is bubbled through the reaction for 15 minutes. The reaction mixture is heated to 40° C. while bubbling nitrogen through the reaction. When reaction reaches 40° C. the bubbling is removed and reaction mixture is stirred at 40° C. for 3 hours under a nitrogen atmosphere. The reaction is cooled to 22° C. and diluted with water (2 L). HCl (5 M) solution is added to adjust the pH to 1. The aqueous layer is separated and washed with additional EtOAc (2×800 mL). The pH of the aqueous layer is adjusted to 10 with sodium hydroxide 50% w/w and then is extracted with EtOAc (10 L). The aqueous layer is washed with additional EtOAc (2×750 mL). The organic extracts are combined, washed with brine, dried over sodium sulfate, filtered, and evaporated to dryness to give the crude title compound as pale yellow solid (124.7 g, 97%). ES/MS (m/e): 356 (M+1).

Preparation 37

N-[7a-(5-Bromo-2-fluoro-phenyl)-4a,5,6,7-tetrahydro-4H-pyrrolo[3,4-d][1,3]thiazin-2-yl]benzamide

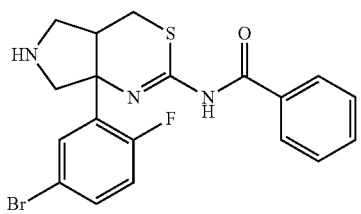 [SMILES: O=C(NC1=NC2(c3cc(Br)ccc3F)CNCC2CS1)c1ccccc1]

Iodotrimethylsilane (2.21 mL, 15.46 mmol) is added dropwise to a room temperature solution of benzyl 2-benzamido-7a-(5-bromo-2-fluoro-phenyl)-4,4a,5,7-tetrahydropyrrolo[3,4-d][1,3]thiazine-6-carboxylate (2.93 g, 5.15 mmol) in acetonitrile (44 mL). The reaction is stirred at room temperature for two hours and the solvent is removed in vacuo. The crude product is purified with an SCX column using 3:1 DCM:methanol and then 2:1 DCM:7 N ammonia in methanol to give the title compound (2.098 g, 94%). ES/MS (m/e): ($^{79}$Br/$^{81}$Br) 434/436 (M+H).

Preparation 38 tert-Butyl (4aR,7aS)-2-benzamido-7a-(3-bromophenyl)-4,4a,5,7-tetrahydropyrrolo[3,4-d][1,3]thiazine-6-carboxylate

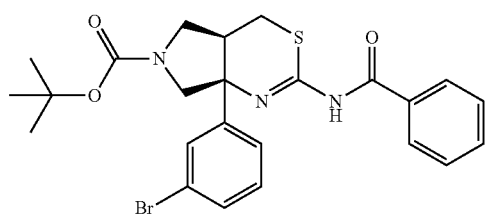 [SMILES: CC(C)(C)OC(=O)N1C[C@H]2CSC(NC(=O)c3ccccc3)=N[C@@]2(c2cccc(Br)c2)C1]

A room temperature solution of N-[(4aR,7aS)-7a-(3-bromophenyl)-4a,5,6,7-tetrahydro-4H-pyrrolo[3,4-d][1,3]thiazin-2-yl]benzamide (22.4 g, 36.69 mmol) in DCM (367 mL) is treated with di-t-butyldicarbonate (8.81 g, 40.36 mmol) followed by triethylamine (7.67 mL, 55.04 mmol) and the reaction is stirred at room temperature for 1 hour under nitrogen. The solvent is removed in vacuo and the crude product is purified over silica gel with a 25 minute 5% to 100% EtOAc in hexanes gradient to give the title compound (20.22 g, 100%). ES/MS (m/e): ($^{79}$Br/$^{81}$Br) 516/518 (M+H).

Preparation 39 tert-Butyl 2-benzamido-7a-(5-bromo-2-fluoro-phenyl)-4,4a,5,7-tetrahydropyrrolo[3,4-d][1,3]thiazine-6-carboxylate

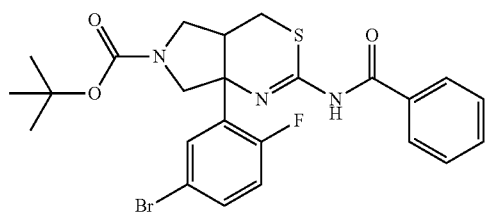 [SMILES: CC(C)(C)OC(=O)N1CC2CSC(NC(=O)c3ccccc3)=NC2(c2cc(Br)ccc2F)C1]

Di-t-butyldicarbonate (1.16 g, 5.31 mmol) and triethylamine (1.01 mL, 7.25 mmol) are added to a solution of N-[7a-(5-bromo-2-fluoro-phenyl)-4a,5,6,7-tetrahydro-4H-pyrrolo[3,4-d][1,3]thiazin-2-yl]benzamide (2.098 g, 4.83 mmol) in DCM (48 mL). The reaction is stirred for 1 hour at room temperature under nitrogen. The solvent is removed in vacuo and the crude product is purified over silica gel with a 30 minute 5% to 100% EtOAc in hexanes gradient to give the title compound (2.556 g, 99%). ES/MS (m/e): ($^{79}$Br/$^{81}$Br) 534/536 (M+H).

Preparation 40 tert-Butyl (4aR,7aS)-7a-(3-aminophenyl)-2-benzamido-4,4a,5,7-tetrahydropyrrolo[3,4-d][1,3]thiazine-6-carboxylate

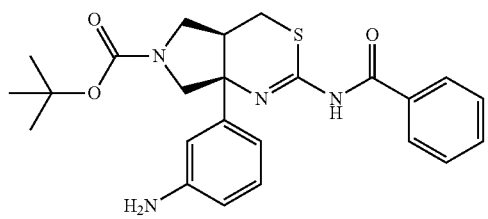 [SMILES: CC(C)(C)OC(=O)N1C[C@H]2CSC(NC(=O)c3ccccc3)=N[C@@]2(c2cccc(N)c2)C1]

A solution of tert-butyl (4aR,7aS)-2-benzamido-7a-(3-bromophenyl)-4,4a,5,7-tetrahydropyrrolo[3,4-d][1,3]thiazine-6-carboxylate (5 g, 9.7 mmol) and trans-N,N'-dimethyl-1,2-cyclohexanediamine (220.3 mg, 1.5 mmol) in ethanol (100 mL) is treated with sodium azide (1.30 g, 19.4 mmol). An aqueous solution of L-ascorbic acid sodium salt (0.66 M, 3.2 mL, 2.1 mmol) and water (10 mL) is added and the top of the flask is purged with nitrogen. The mixture is treated with an aqueous solution of copper(II)sulfate pentahydrate (0.33 M, 3.2 mL, 1.1 mmol) and the mixture is immediately heated on a preheated hot plate at 80° C. for 1.5 hours under nitrogen. A homogeneous mixture is obtained upon heating. The reaction is cooled and ice water is added. The mixture is extracted with EtOAc (3×). The organic layers are combined and dried over sodium sulfate, filtered, and the solvent is removed in vacuo to give crude azide product. The crude azide product is combined with 10% palladium on carbon (2 g) in cold ethanol (150 mL) and the mixture is purged using vacuum/nitrogen and then vacuum/hydrogen. The mixture is stirred at room temperature under 30 psi of hydrogen for 2 hours. The reaction is vented and the mixture is filtered through diatomaceous earth using DCM to rinse the filter cake. The solvent is removed from the filtrate in vacuo and the crude product is purified over silica gel with 50% EtOAc in DCM to give the title compound (4 g, 91%). ES/MS (m/e): 453 (M+H).

Preparation 41 tert-Butyl 7a-(5-amino-2-fluoro-phenyl)-2-benzamido-4,4a,5,7-tetrahydropyrrolo[3,4-d][1,3]thiazine-6-carboxylate

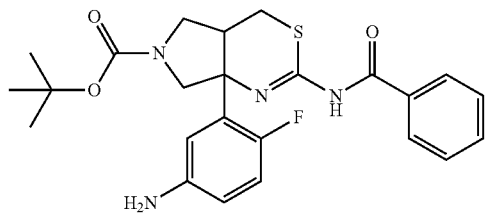 [SMILES: CC(C)(C)OC(=O)N1CC2CSC(NC(=O)c3ccccc3)=NC2(c2cc(N)ccc2F)C1]

A solution of tert-butyl 2-benzamido-7a-(5-bromo-2-fluoro-phenyl)-4,4a,5,7-tetrahydropyrrolo[3,4-d][1,3]thiazine-6-carboxylate (2.556 g, 4.8 mmol) and trans-N,N'-dimethyl-1,2-cyclohexanediamine (150 mg, 1.1 mmol) in ethanol (50 mL) is treated with sodium azide (933 mg, 14.3 mmol). An aqueous solution of L-ascorbic acid sodium salt (0.66 M, 3.2 mL, 2.1 mmol) and water (1 mL) are added and the top of the flask is purged with nitrogen. The mixture is treated with an aqueous solution of copper(II)sulfate pentahydrate (0.33 M, 3.2 mL, 1.1 mmol) and the mixture is immediately heated on a preheated hot plate at 80° C. for 1.5 hrs under nitrogen. A homogeneous mixture is obtained upon heating. The reaction is cooled, diluted with ice water, and the mixture is extracted with EtOAc (3×). The organic extracts are combined and dried over sodium sulfate, filtered, and the solvent removed in vacuo to give the crude azide product. The crude azide product is combined with 10% palladium on carbon (1 g) in cold ethanol (150 mL) and the mixture is purged using vacuum/nitrogen and then vacuum/hydrogen. The mixture is stirred at room temperature under 30 psi of hydrogen for 5 hours. The reaction is vented, filtered through diatomaceous earth, and the filter cake rinsed with DCM. The solvent is removed from the filtrate in vacuo and the crude product is purified over silica gel with 50% EtOAc in DCM to give the title compound (2.014 g, 89%). ES/MS (m/e): 471 (M+H).

Preparation 42 tert-Butyl (4aR,7aS)-2-benzamido-7a-[3-[(5-fluoro-pyridine-2-carbonyl)amino]phenyl]-4,4a,5,7-tetrahydropyrrolo[3,4-d][1,3]thiazine-6-carboxylate

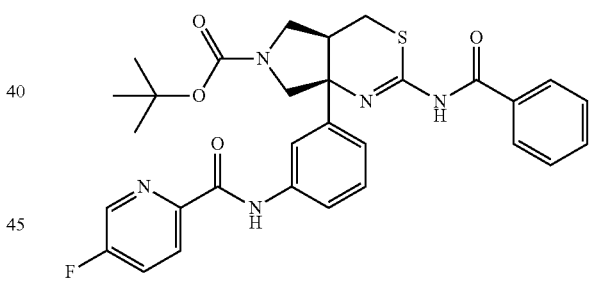

A slurry of tert-butyl (4aR,7aS)-7a-(3-aminophenyl)-2-benzamido-4,4a,5,7-tetrahydropyrrolo[3,4-d][1,3]thiazine-6-carboxylate (93 mg, 0.21 mmol), 5-fluoropyridine-2-carboxylic acid (31.9 mg, 0.23 mmol), 1-hydroxybenzotriazole hydrate (56.7 mg, 0.41 mmol) and EDCI (40 mg, 0.21 mmol) in DCM (4 mL) containing dimethylformamide (1 ml) is treated with DIPEA (179.2 µL, 1.03 mmol) and the resulting mixture is stirred at room temperature overnight. The reaction mixture is diluted with DCM (5 mL) and saturated aqueous sodium bicarbonate (15 mL). The organic layer is separated and washed with saturated aqueous sodium chloride (10 mL), dried over sodium sulfate, filtered, and the solvent removed in vacuo to give the crude title compound (105 mg, 89%). ES/MS (m/e): 576 (M+H).

Preparation 43

N-[3-[(4aR,7aS)-2-Benzamido-4a,5,6,7-tetrahydro-4H-pyrrolo[3,4-d][1,3]thiazin-7a-yl]phenyl]-5-fluoro-pyridine-2-carboxamide; 2,2,2-trifluoroacetic acid

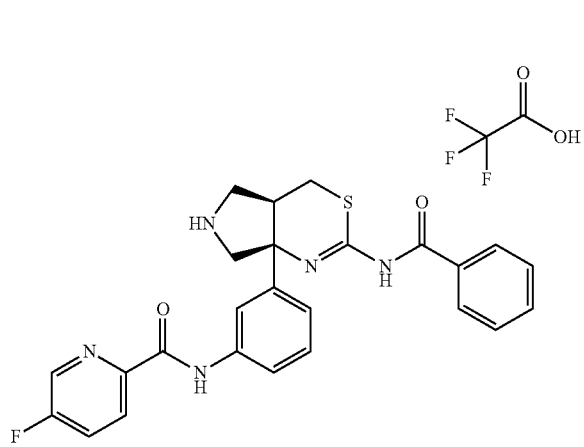

tert-Butyl (4aR,7aS)-2-benzamido-7a-[3-[(5-fluoropyridine-2-carbonyl)amino]phenyl]-4,4a,5,7-tetrahydropyrrolo[3,4-d][1,3]thiazine-6-carboxylate (105 mg, 0.18 mmol) is dissolved in DCM (2 mL) and treated with trifluoroacetic acid (500 μL, 6.6 mmol). The resulting yellow solution is stirred for 4 hours at room temperature and the solvent removed in vacuo to give the crude title product (190 mg, 100%). ES/MS (m/e): 476 (M+H).

Preparation 44

N-[(4aR,7aS)-7a-(3-Aminophenyl)-4a,5,6,7-tetrahydro-4H-pyrrolo[3,4-d][1,3]thiazin-2-yl]benzamide

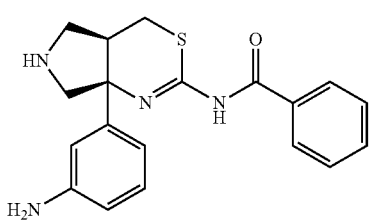 [SMILES: Nc1cccc([C@]23CNC[C@H]2CSC(NC(=O)c2ccccc2)=N3)c1]

Trifluoroacetic acid (25 mL) is added to a solution of tert-butyl (4aR,7aS)-7a-(3-aminophenyl)-2-benzamido-4,4a,5,7-tetrahydropyrrolo[3,4-d][1,3]thiazine-6-carboxylate (4 g, 8.84 mmol) in DCM (100 mL) and the mixture is stirred at room temperature under nitrogen for 4 hours. The solvent is removed in vacuo and the crude product is purified with an SCX column using 3:1 DCM:methanol and then 2:1 DCM:7 N ammonia in methanol to give the title compound (2.49 g, 80%). ES/MS (m/e): 353 (M+H).

Preparation 45

N-[7a-(5-Amino-2-fluoro-phenyl)-4a,5,6,7-tetrahydro-4H-pyrrolo[3,4-d][1,3]thiazin-2-yl]benzamide

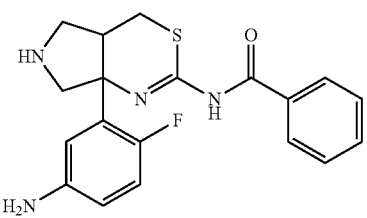 [SMILES: Nc1ccc(F)c(C23CNCC2CSC(NC(=O)c2ccccc2)=N3)c1]

Trifluoroacetic acid (10 mL) is added to a solution of tert-butyl 7a-(5-amino-2-fluoro-phenyl)-2-benzamido-4,4a,5,7-tetrahydropyrrolo[3,4-d][1,3]thiazine-6-carboxylate (2.013 g, 4.28 mmol) in DCM (30 mL) and the mixture is stirred at room temperature under nitrogen for 4 hours. The solvent removed in vacuo and the crude product is purified with an SCX column using 3:1 DCM:methanol and then 2:1 DCM:7 N ammonia in methanol to give the title compound (1.555 g, 98%). ES/MS (m/e): 371 (M+H).

Preparation 46

N-[(4aR,7aS)-7a-(3-Aminophenyl)-6-(5-fluoropyrimidin-2-yl)-4,4a,5,7-tetrahydropyrrolo[3,4-d][1,3]thiazin-2-yl]benzamide

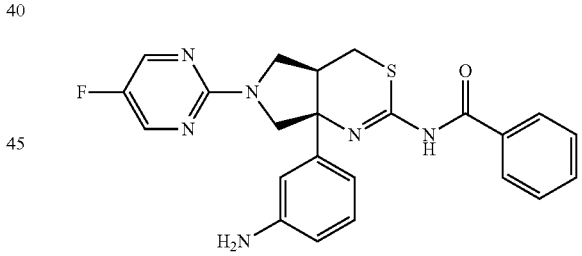

A solution of N-[(4aR,7aS)-7a-(3-aminophenyl)-4a,5,6,7-tetrahydro-4H-pyrrolo[3,4-d][1,3]thiazin-2-yl]benzamide (2.49 g, 7.06 mmol), 5-fluoro-2-chloropyrimidine (3.74 g, 28.26 mmol), and DIPEA (6.16 mL, 35.32 mmol) in 1,4-dioxane (60 mL) is heated to reflux for 4 hours under nitrogen. The reaction is cooled, diluted with water, and extracted with EtOAc (3×). The combined organic extracts are dried over sodium sulfate, filtered and the solvent is removed in vacuo to give the crude product. The crude product is purified over silica gel with a 25 minute 5% to 100% EtOAc in hexanes gradient to give the title compound (2.51 g, 79%). ES/MS (m/e): 449 (M+H).

Preparation 47

N-[(4aR,7aS)-7a-(2-Fluorophenyl)-6-(5-fluoropyrimidin-2-yl)-4,4a,5,7-tetrahydropyrrolo[3,4-d][1,3]thiazin-2-yl]benzamide

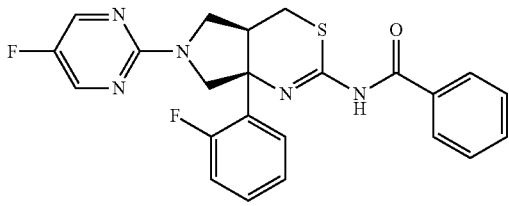 [SMILES: O=C(NC1=N[C@@]2(c3ccccc3F)CN(c3ncc(F)cn3)C[C@H]2CS1)c1ccccc1]

A solution of N-[(4aR,7aS)-7a-(2-fluorophenyl)-4a,5,6,7-tetrahydro-4H-pyrrolo[3,4-d][1,3]thiazin-2-yl]benzamide (124.7 g, 256 mmol), DIPEA (67 mL), 5-fluoro-2-chloropyrimidine (29.3 ml, 307 mmol) in N-methylpyrrolidone (997 mL) is heated to 100° C. for 16 hours. The reaction is cooled to 22° C. and poured into cooled water at 10° C. (10 L) keeping temperature below 15° C. A pale cream solid is collected by filtration and washed with additional water. The wet solid is dissolved in EtOAc (2 L) and transferred to a separator funnel. Sodium chloride aqueous solution 5% w/w (1 L) is added and the organic layer is separated, dried over sodium sulfate, filtered, and the filtrate evaporated under reduced pressure. The product is purified by silica gel chromatography using a gradient of 0-40% EtOAc/isohexane to give the title compound as a pale yellow solid (116 g, 70%). ES/MS (m/e): 452 (M+1).

Preparation 48

N-((4aR,7aS)-7a-(5-Acetamido-2-fluorophenyl)-6-(5-fluoropyrimidin-2-yl)-4,4a,5,6,7,7a-hexahydropyrrolo[3,4-d][1,3]thiazin-2-yl)benzamide

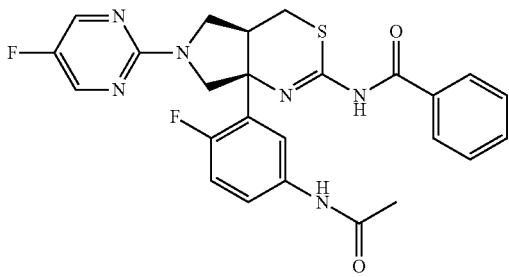 [SMILES: CC(=O)Nc1ccc(F)c([C@]23CN(c4ncc(F)cn4)C[C@H]2CSC(NC(=O)c2ccccc2)=N3)c1]

2-Chloro-5-fluoropyrimidine (28.9 g, 218 mmol) and potassium carbonate (33.46 g, 242.1 mmol) are added to a solution of N-((4aR,7aS)-7a-(5-acetamido-2-fluorophenyl)-4,4a,5,6,7,7a-hexahydropyrrolo[3,4-d][1,3]thiazin-2-yl)benzamide (50 g, 121.22 mmol) in DMF (100 mL). The mixture is heated to 80-85° C. for 8 hours. The mixture is cooled to 24° C., filtered, and washed with DMF (100 mL). The solids are slurried in water (2 L) and filtered to obtain the title compound (68.5 g, 98%). LC-MS: m/z=509.2 (M+1)+, $^1$H NMR (400 MHz, d$_6$-DMSO) δ ppm 1.22 (t, J=7.28 Hz, 2H) 1.92-2.07 (m, 6H) 2.89-3.20 (m, 2H) 3.36-3.44 (m, 1H) 3.67 (t, J=9.54 Hz, 1H) 3.84 (br. s., 1H) 4.16 (br. s., 2H) 7.23 (br. s., 2H) 7.35-7.61 (m, 8H) 7.77 (br. s., 2H) 7.85-8.18 (m, 4H) 8.48 (s, 4H) 10.15 (br. s., 1H) 10.46-10.59 (m, 1H).

Preparation 49

(4aR,7aS)-7a-(5-Amino-2-fluorophenyl)-6-(5-fluoropyrimidin-2-yl)-4,4a,5,6,7,7a-hexahydropyrrolo[3,4-d][1,3]thiazin-2-amine

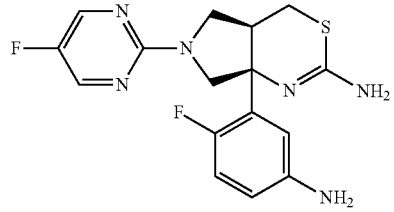 [SMILES: NC1=N[C@@]2(c3cc(N)ccc3F)CN(c3ncc(F)cn3)C[C@H]2CS1]

Lithium hydroxide (8.6 g, 204.9 mmol) is added to a solution of N-((4aR,7aS)-7a-(5-acetamido-2-fluorophenyl)-6-(5-fluoropyrimidin-2-yl)-4,4a,5,6,7,7a-hexahydropyrrolo[3,4-d][1,3]thiazin-2-yl)benzamide (80 g, 157.3 mmol) in methanol (400 mL). The mixture is heated to 60-70° C. for 4 hours. Concentrated HCl (132 g) is added and the mixture is stirred at 55° C. for 18 hours. The mixture is cooled to 30° C. and concentrated to remove the methanol. Water is added and the aqueous layer is extracted with DCM (3×) to obtain the title compound as an aqueous solution of 920 g of which 5.6% of the total mass is the title compound which is used without further purification.

Preparation 50

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-5-fluoro-pyridine-2-carboxamide

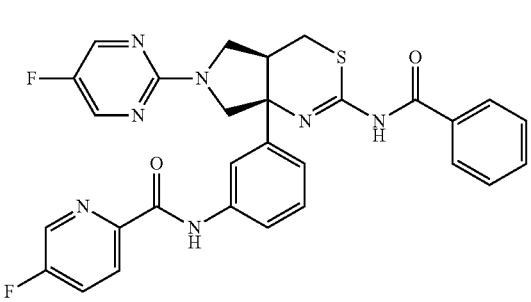 [SMILES: O=C(NC1=N[C@@]2(c3cccc(NC(=O)c4ccc(F)cn4)c3)CN(c3ncc(F)cn3)C[C@H]2CS1)c1ccccc1]

A solution of N-[3-[(4aR,7aS)-2-benzamido-4a,5,6,7-tetrahydro-4H-pyrrolo[3,4-d][1,3]thiazin-7a-yl]phenyl]-5-fluoro-pyridine-2-carboxamide; 2,2,2-trifluoroacetic acid (150 mg, 254 μmol), 5-fluoro-2-chloropyrimidine (68 mg, 51 μmol) and DIPEA (98 μL, 56 μmol) is heated in DMSO (5 mL) overnight at 40° C. Additional 5-fluoro-2-chloropyrimidine (68 mg, 51 μmol) and DIPEA (98 pt, 56 μmol) is added and the mixture is heated overnight at 50° C. Additional 5-fluoro-2-chloropyrimidine (68 mg, 51 μmol) and DIPEA (98 pt, 56 μmol) is added and the mixture is heated overnight at 50° C. for a third night. The reaction is cooled, diluted with saturated aqueous sodium carbonate (50 mL) to give a slurry that is filtered and dried in a vacuum oven at 50° C. for 4 hours to give the title compound (60 mg, 41%). ES/MS (m/e): 449 (M+H).

Alternate Preparation 50

N-[(4aR,7aS)-7a-(3-Aminophenyl)-6-(5-fluoropyrimidin-2-yl)-4,4a,5,7-tetrahydropyrrolo[3,4-d][1,3]thiazin-2-yl]benzamide (282 mg, 628.73 μmol) and 5-fluoropyridine-2-carboxylic acid (106.46 mg, 754.47 μmol) are combined in DCM (3 mL) and dimethylformamide (0.5 mL). HOBT (112.70 mg, 817.35 μmol) and then EDCI (159.07 mg, 817.35 μmol) are added and the resulting mixture is stirred for 5 hours at room temperature under nitrogen. The reaction mixture is diluted with water and the pH is adjusted with 1 N NaOH to ~12. The mixture is extracted with EtOAc (3×). The organic extracts are combined, dried over sodium sulfate, filtered and the solvent removed in vacuo to give the crude product. The crude product is purified over silica gel with a 20 minute 5% to 100% EtOAc in hexanes gradient to give the title compound (327 mg, 91%). ES/MS (m/e): 571 (M+H).

Preparation 51

N-[7a-(5-Amino-2-fluoro-phenyl)-6-(5-fluoropyrimidin-2-yl)-4,4a,5,7-tetrahydropyrrolo[3,4-d][1,3]thiazin-2-yl]benzamide

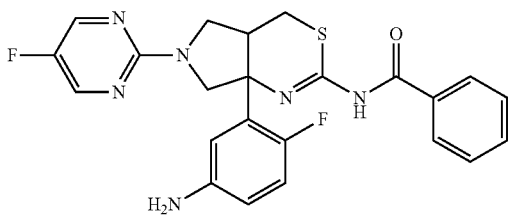 [SMILES: Nc1ccc(F)c(C23CN(c4ncc(F)cn4)CC2CSC(NC(=O)c2ccccc2)=N3)c1]

A solution of N-[7a-(5-amino-2-fluoro-phenyl)-4a,5,6,7-tetrahydro-4H-pyrrolo[3,4-d][1,3]thiazin-2-yl]benzamide (705 mg, 1.90 mmol), 5-fluoro-2-chloropyrimidine (1.01 g, 7.61 mmol), and DIPEA (1.66 mL, 9.52 mmol) are heated in 1,4-dioxane (20 mL) to reflux for 4 hours under nitrogen. The reaction is cooled, diluted with water, and extracted with EtOAc (3×). The organic layers are combined, dried over sodium sulfate, filtered and the solvent removed in vacuo to give crude product. The crude product is purified over silica gel with a 25 minute 5% to 100% EtOAc in hexanes gradient to give the title compound (590 mg, 66%). ES/MS (m/e): 467 (M+H).

Preparation 52

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-5-methoxy-pyrazine-2-carboxamide

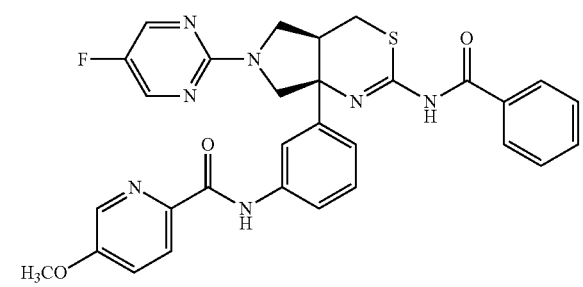 [SMILES: COc1ccc(C(=O)Nc2cccc([C@]34CN(c5ncc(F)cn5)C[C@H]3CSC(NC(=O)c3ccccc3)=N4)c2)nc1]

N-[(4aR,7aS)-7a-(3-Aminophenyl)-6-(5-fluoropyrimidin-2-yl)-4,4a,5,7-tetrahydropyrrolo[3,4-d][1,3]thiazin-2-yl]benzamide (400 mg, 891.81 μmole) and 5-methoxypyrazine-2-carboxylic acid (165 mg, 1.07 mmol) are combined in DCM (4 mL) and dimethylformamide (0.5 mL). HOBt (160 mg, 1.16 mmol) and then EDCI (226 mg, 1.16 mmol) are added and the resulting mixture is stirred for 5 hours at room temperature under nitrogen. The reaction mixture is diluted with water and the pH is adjusted to ~12 with 1 N NaOH. The mixture is extracted with EtOAc (3×). The combined organic extracts are dried over sodium sulfate, filtered and the solvent removed in vacuo. The crude product is purified over silica gel with a 20 minute 5% to 100% EtOAc in hexanes gradient to give the title compound (482 mg, 92%). ES/MS (m/e): 585 (M+H).

Preparation 53

N-[3-[2-Benzamido-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide

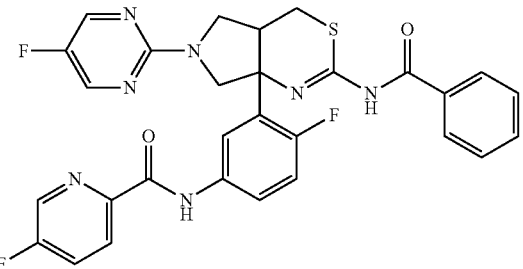

N-[7a-(5-Amino-2-fluoro-phenyl)-6-(5-fluoropyrimidin-2-yl)-4,4a,5,7-tetrahydropyrrolo[3,4-d][1,3]thiazin-2-yl]benzamide (302 mg, 647 μmol) and 5-fluoropyridine-2-carboxylic acid (110 mg, 777 μmol) are combined in DCM (3 mL) and dimethylformamide (0.5 mL). HOBT (116 mg, 842 μmol) and then EDCI (164 mg, 842 μmol) are added and the mixture is stirred overnight at room temperature under nitrogen. The reaction mixture is diluted with water and the pH adjusted with 1 N NaOH to ~12 and then extracted with EtOAc (3×). The organic layers are combined and filtered to collect the insoluble material. The solids are washed with water and EtOAc and dried under vacuum to give the title compound. The organic layer from the filtrate is dried over sodium sulfate, filtered, and the solvent removed in vacuo. The residue is purified over silica gel with a 20 minute 5% to 100% EtOAc in hexanes gradient to give additional title compound with a combined yield (275 mg, 72%). ES/MS (m/e): 590 (M+H).

Preparation 54

N-[(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-yl]benzamide, (isomer 1)

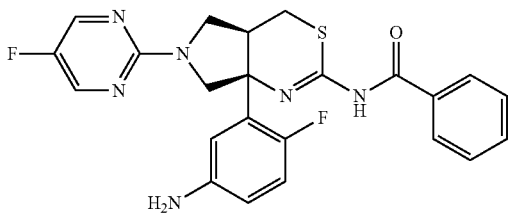 [SMILES: Nc1ccc(F)c([C@]23CN(c4ncc(F)cn4)C[C@H]2CSC(NC(=O)c2ccccc2)=N3)c1]

Racemic N-[7a-(5-amino-2-fluoro-phenyl)-6-(5-fluoropyrimidin-2-yl)-4,4a,5,7-tetrahydropyrrolo[3,4-d][1,3]thiazin-2-yl]benzamide (1.694 g, 3.63 mmol) is purified by chiral HPLC (Column: Chiralcel OJ, 8×35 cm; eluent: 90% methanol (0.2% dimethylethylamine) and 10% acetonitrile; flow 400 mL/min at UV 280 nm). Analysis of the first eluting isomer (Column: Chiralcel OJ-H 0.46×15 cm; eluent: 10:90 acetonitrile:methanol (with 0.2% dimethylethylamine); flow: 0.6 mL/min at UV 280 nm) confirms the enantiomerically enriched (99% ee) enantiomer with $R_t$=6.70 minutes, (723 mg, 43%). ES/MS (m/e): 467 (M+H).

Preparation 55

N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide, (isomer 1)

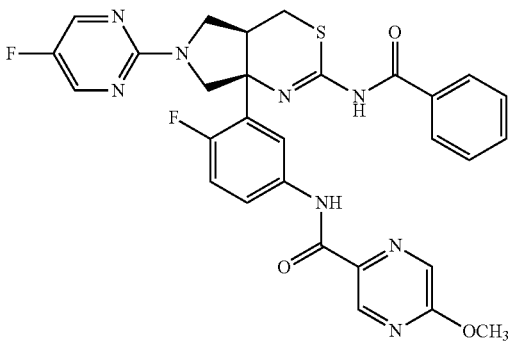 [SMILES: COc1cnc(C(=O)Nc2ccc(F)c([C@]34CN(c5ncc(F)cn5)C[C@H]3CSC(NC(=O)c3ccccc3)=N4)c2)cn1]

N-[(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-yl]benzamide (0.361 g, 0.77 mmol, isomer 1) is dissolved in a mixture of DCM (4 mL) and DMF (0.5 mL). 5-Methoxypyrazine-2-carboxylic acid (240 mg, 1.55 mmol), HOBT (210 mg, 1.55 mmol) and EDCI (300 mg, 1.55 mmol) are added to the mixture and the mixture is stirred overnight at room temperature. The reaction solution is added directly onto a 12 g silica gel loading column and purified using a 40 g silica gel column and eluting with a 0-100% EtOAc/hexanes gradient. The product is dissolved in EtOAc (200 mL), washed with 1 N NaOH (2×50 mL), and with brine (1×50 mL). The silica gel purification is repeated as described above to give the title compound (350 mg, 74%). ES/MS (m/e): 603 (M+H).

Preparation 56

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-5-cyano-pyridine-2-carboxamide

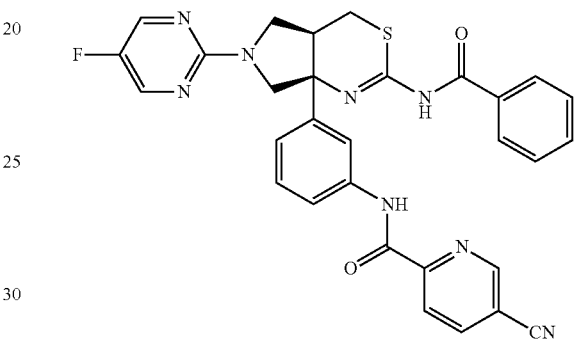

N-[(4aR,7aS)-7a-(3-Aminophenyl)-6-(5-fluoropyrimidin-2-yl)-4,4a,5,7-tetrahydropyrrolo[3,4-d][1,3]thiazin-2-yl]benzamide (0.30 g, 0.67 mmol) is dissolved in DCM (10 mL) and 5-cyanopyridine-2-carboxylic acid (129 mg, 0.87 mmol), HOBt (185 mg, 1.34 mmol) and EDCI (169 mg, 0.87 mmol) are added. DIPEA (0.35 mL, 2 mmol) is added and the reaction is stirred at room temperature overnight. The material is purified directly with silica gel chromatography eluting with a 0-100% EtOAc/hexanes gradient to give the title compound (360 mg, 88%). ES/MS (m/e): 579 (M+H).

Preparation 57

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-3,5-difluoro-pyridine-2-carboxamide

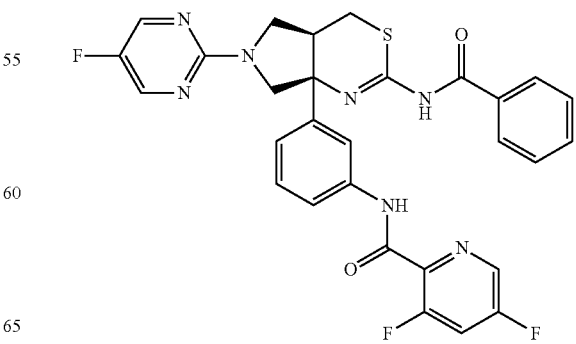

N-[(4aR,7aS)-7a-(3-Aminophenyl)-6-(5-fluoropyrimidin-2-yl)-4,4a,5,7-tetrahydropyrrolo[3,4-d][1,3]thiazin-2-yl]benzamide (0.30 g, 0.67 mmol) is dissolved in DCM (10 mL) and 3,5-difluoropyridine-2-carboxylic acid (138 mg, 0.87 mmol), HOBT (185 mg, 1.34 mmol) and EDCI (169 mg, 0.87 mmol) are added. Dipea (0.35 mL, 2 mmol) is added and the reaction is stirred at room temperature overnight. The reaction is purified directly with silica gel chromatography eluting with a 0-100% EtOAc/hexanes gradient to give the title compound (330 mg, 84%). ES/MS (m/e): 590 (M+H).

Preparation 58

N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-5-cyano-pyridine-2-carboxamide, (isomer 1)

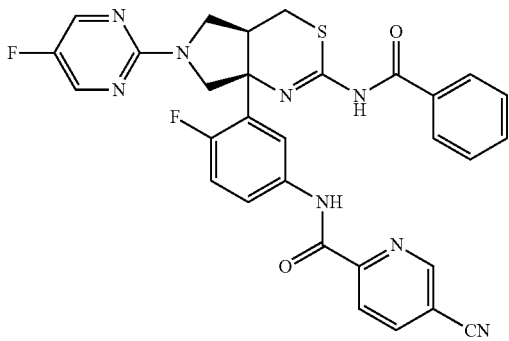 [SMILES: N#Cc1ccc(C(=O)Nc2ccc(F)c([C@]34CN(c5ncc(F)cn5)C[C@H]3CSC(NC(=O)c3ccccc3)=N4)c2)nc1]

N-[(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-yl]benzamide (0.180 g, 0.39 mmol, isomer 1) is dissolved in a mixture of DCM (2 mL) and DMF (0.25 mL). 5-Cyanopyridine-2-carboxylic acid (114 mg, 0.77 mmol), HOBt (106 mg, 0.77 mmol) and EDCI (150 mg, 0.77 mmol) are added and the reaction is stirred at room temperature overnight. The mixture is diluted with water (10 mL), EtOAc (10 mL) and added to a solution of 1 N NaOH (100 mL). The mixture is extracted with EtOAc (2×100 mL) and the organic layers are combined and washed with brine. The organic layer is dried over MgSO$_4$, filtered, and concentrated. The residue is purified over silica gel chromatography using a 0-100% EtOAc/hexanes gradient to give the title compound (133 mg, 57%). ES/MS (m/e): 597 (M+H).

Preparation 59

N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-3,5-difluoro-pyridine-2-carboxamide, (isomer 1)

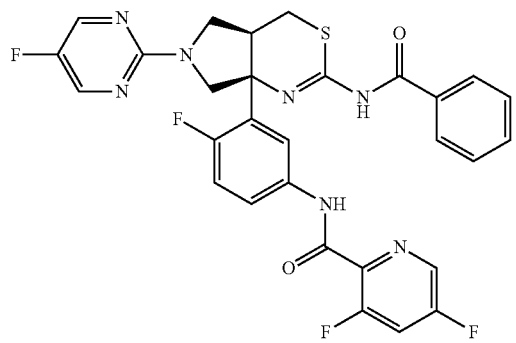 [SMILES: O=C(NC1=N[C@@]2(c3cc(NC(=O)c4ncc(F)cc4F)ccc3F)CN(c3ncc(F)cn3)C[C@H]2CS1)c1ccccc1]

N-[(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-yl]benzamide (0.180 g, 0.39 mmol, isomer 1) is dissolved in a mixture of DCM (2 mL) and DMF (0.25 mL). 5-Cyanopyridine-2-carboxylic acid (114 mg, 0.77 mmol), HOBt (106 mg, 0.77 mmol) and EDCI (150 mg, 0.77 mmol) are added and the reaction is stirred at room temperature overnight. The mixture is diluted with water (10 mL) and EtOAc (10 mL) and then poured into a solution of 1 N NaOH (100 mL). The mixture is extracted with EtOAc (2×100 mL) the organic extracts are combined and washed with brine. The organic layers are dried over MgSO$_4$, filtered, and concentrated. The residue is purified via silica gel chromatography using a 0-100% EtOAc/hexanes gradient to give the title compound (190 mg, 80%). ES/MS (m/e): 608 (M+H).

Preparation 60

(4aR,7aS)-7a-(2-Fluorophenyl)-6-(5-fluoropyrimidin-2-yl)-4,4a,5,7-tetrahydropyrrolo[3,4-d][1,3]thiazin-2-amine

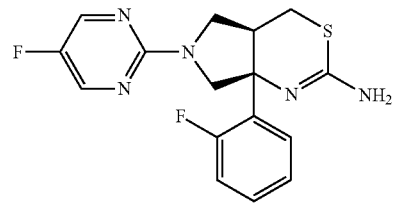 [SMILES: NC1=N[C@@]2(c3ccccc3F)CN(c3ncc(F)cn3)C[C@H]2CS1]

Lithium hydroxide (9.26 g, 386 mmol) is added to a mixture of N-[(4aR,7aS)-7a-(2-fluorophenyl)-6-(5-fluoropyrimidin-2-yl)-4,4a,5,7-tetrahydropyrrolo[3,4-d][1,3]thiazin-2-yl]benzamide (158.6 g, 351.6 mmol), in methanol (1.6 L). The mixture is heated at 70° C. for 4 hours and then cooled to 22° C. The reaction mixture is evaporated under vacuum to a yellow residue. The residue is partitioned in water (1 L) and EtOAc (750 mL). HCl (5 M aqueous solution) is added to adjust the pH to 1. The aqueous layer is separated and the organic layer is washed with EtOAc

Preparation 61

(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-amine

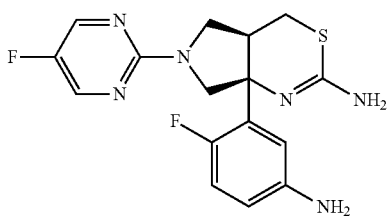 [SMILES: NC1=N[C@@]2(c3cc(N)ccc3F)CN(c3ncc(F)cn3)C[C@H]2CS1]

Sulfuric acid (33.4 ml, 626.6 mmol) is added to a solution of (4aR,7aS)-7a-(2-fluorophenyl)-6-(5-fluoropyrimidin-2-yl)-4,4a,5,7-tetrahydropyrrolo[3,4-d][1,3]thiazin-2-amine (45.8 g, 125.3 mmol) in trifluoroacetic acid (626 mL). The mixture is cooled to 0° C. and stirred for 20 minutes. Fuming nitric acid (6.2 mL, 144.1 mmol) is added and the reaction mixture is warmed to 22° C. and stirred at for 3 hours. The reaction mixture is evaporated and MTBE is added (250 mL) and evaporated twice. The residue is dried under vacuum to a constant weight and then is dissolved in water (147 mL) and ethanol (885 mL) and degassed with bubbling nitrogen for 15 minutes. The solution is transferred to a pressure reactor and 10% Pd/C paste type 87 L (6.6 g, 6.27 mmol) is added. The mixture is diluted with additional ethanol (700 mL) and pressurized with hydrogen at 80 psi for 16 hours. The reaction mixture is filtered and then a second catalyst charge is added of 10% Pd/C paste type 87 L (6.6 g, 6.27 mmol) and the mixture is pressurized to 80 psi and stirred for 3 days in the pressure reactor. The reaction mixture is purged with nitrogen and filtered over diatomaceous earth. The filtrate is evaporated and the residue is partitioned between water (200 ml) and EtOAc (200 ml). The aqueous layer is separated, cooled to 5° C., and neutralized with ammonium hydroxide 15% w/w. The aqueous layer is extracted with EtOAc (3×150 mL). The organics are combined, dried over sodium sulfate, filtered, and evaporated under reduced pressure to give the title compound as light brown solid (47.7 g, 99% containing residual EtOAc). ES/MS (m/e): 363 (M+1).

Example A

N-[3-[2-Amino-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide

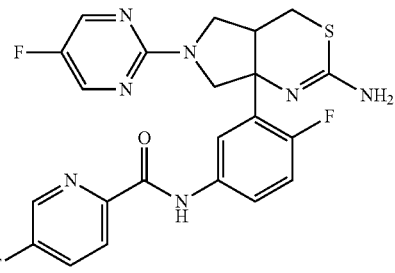

A mixture of N-[3-[2-benzamido-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide (293 mg, 497 μmol), O-methylhydroxylamine hydrochloride (430 mg, 4.97 mmol) and pyridine (402 μL, 4.97 mmol) is heated in ethanol (13 mL) to 70° C. in a capped flask for 2.5 hours. DMSO (3 mL) is added and the mixture is heated at 70° C. overnight. Additional DMSO (10 mL) is added and heating continued at 70° C. for 4 hours. Additional O-methylhydroxylamine hydrochloride (208 mg, 2.48 mmol) and pyridine (201 μL, 2.48 mmol) is added and the mixture is heated to 60° C. for 3 hours and the mixture is stirred for 3 days at room temperature. In a separate flask, a mixture of N-[3-[2-benzamido-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide (276 mg, 468 μmol), O-methylhydroxylamine hydrochloride (405 mg, 4.68 mmol) and pyridine (478 μL, 4.68 mmol) is heated in ethanol (15 mL) and DMSO (4 mL) at 70° C. in a capped flask overnight. Additional DMSO (10 mL) is added and heating is continued at 70° C. for 4 hours. Additional O-methylhydroxylamine hydrochloride (195 mg, 2.34 mmol) and pyridine (189 μL, 2.34 mmol) is added and heating continued at 70° C. for 3 hours followed by stirring the mixture for 3 days at room temperature. The two reaction mixtures are combined and most of the solvent removed in vacuo. The crude product is purified on a SCX column using 3:1 DCM:methanol and then 2:1 DCM:7 N ammonia in methanol. The crude product is further purified over silica gel with a 20 minute 0.5% to 10% gradient of 7 N ammonia methanol in DCM gradient to give the title compound (451 mg, 96%). ES/MS (m/e): 486 (M+H).

Example 1

N-{3-[(4aR,7aS)-2-Amino-6-(5-fluoropyrimidin-2-yl)-4a,5,6,7-tetrahydropyrrolo[3,4-d][1,3]thiazin-7a(4H)-yl]phenyl}-5-fluoropyridine-2-carboxamide hydrochloride

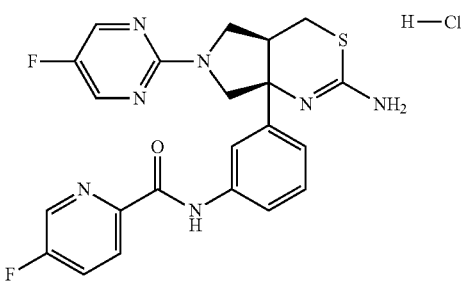 [SMILES: NC1=N[C@@]2(c3cccc(NC(=O)c4ccc(F)cn4)c3)CN(c3ncc(F)cn3)C[C@H]2CS1 ; Cl]

A mixture of N-[3-[(4aR,7aS)-2-benzamido-6-(5-fluoropyrimidin-2-yl)-4a,5,7-tetrahydropyrrolo[3,4-d][1,3]thiazin-7a-yl]phenyl]-5-fluoro-pyridine-2-carboxamide (320 mg, 560 μmol), O-methylhydroxylamine hydrochloride (485 mg, 5.60 mmol) and pyridine (453 μL, 5.60 mmol) in ethanol (15 mL) is heated at 65° C. in a capped vial for five hours. The reaction is cooled and the solvent removed in vacuo. The crude product is purified over silica gel with a 30 minute 0.5% to 10% gradient of 7 N ammonia in methanol DCM gradient to give N-[3-[(4aR,7aS)-2-amino-6-(5-fluoropyrimidin-2-yl)-4,4a,5,7-tetrahydropyrrolo[3,4-d][1,3]thiazin-7a-yl]phenyl]-5-fluoro-pyridine-2-carboxamide (219 mg, 84%). This material is dissolved in DCM (1 mL) and methanol (0.5 mL) and 1 M hydrogen chloride in diethyl ether (0.47 mL, 470 μmol) is added. The solvent is removed in vacuo to give the title compound (228 mg, 81%). ES/MS (m/e): 468 (M+H).

Example 2

N-{3-[(4aR,7aS)-2-Amino-6-(5-fluoropyrimidin-2-yl)-4a,5,6,7-tetrahydropyrrolo[3,4-d][1,3]thiazin-7a(4H)-yl]phenyl}-5-methoxypyrazine-2-carboxamide hydrochloride

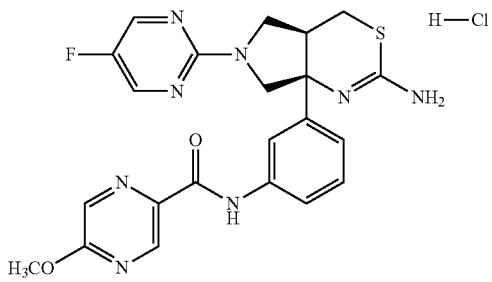

A mixture of N-[3-[(4aR,7aS)-2-benzamido-6-(5-fluoropyrimidin-2-yl)-4,4a,5,7-tetrahydropyrrolo[3,4-d][1,3]thiazin-7a-yl]phenyl]-5-methoxy-pyrazine-2-carboxamide (479 mg, 819 μmol), O-methylhydroxylamine hydrochloride (709 mg, 8.19 mmol) and pyridine (663 μL, 8.19 mmol) in ethanol (20 mL) is heated at 50° C. in a capped flask overnight. DMSO (4 mL) is added and the mixture is heated to 70° C. for 4 hours to obtain a solution. The reaction is cooled and most of the solvent is removed in vacuo. Water is added and the pH is adjusted to ~12 with 1 N sodium hydroxide. The mixture is extracted with EtOAc (5×). The combined organic extracts are dried over sodium sulfate, filtered and the solvent removed in vacuo. The crude product is purified over silica gel with a 30 minute 0.5% to 10% gradient of 7 N ammonia methanol in DCM gradient. The mixture is purified again on a SCX column using 3:1 DCM:methanol and then 2:1 DCM:7 N ammonia in methanol to remove residual DMSO. The mixture is purified a final time over silica gel with a 20 minute 0.5% to 10% gradient of 7 N ammonia methanol in DCM to give N-[3-[(4aR,7aS)-2-amino-6-(5-fluoropyrimidin-2-yl)-4,4a,5,7-tetrahydropyrrolo[3,4-d][1,3]thiazin-7a-yl]phenyl]-5-methoxy-pyrazine-2-carboxamide. This material is dissolved in DCM (1 mL) and methanol (0.5 mL) and 1 M hydrogen chloride in diethyl ether (0.66 mL, 660 μmol) is added. The solvent is removed in vacuo to give the title compound (329 mg, 78%). ES/MS (m/e): 481 (M+H).

Example 3

N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide hydrochloride

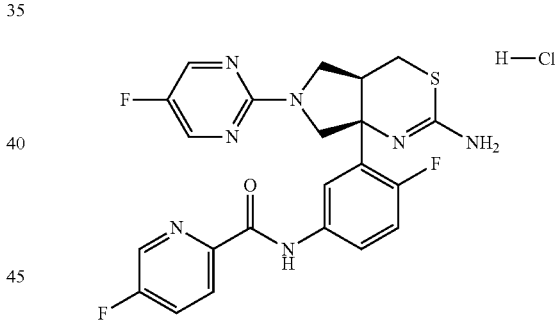

Racemic N-[3-[2-amino-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide (451 mg, 929 μmol) is chirally purified by SFC (Column: Chiralcel OD-H (5 um), 2.1×25 cm; eluent: 40% methanol (0.2% isopropylamine) in $CO_2$; flow 70 mL/min at UV 225 nm). Chiral analysis of the first eluting isomer: Column: Chiralcel OD-H (5 μm), 4.6×150 mm; eluent: 40% methanol (0.2% isopropylamine) in $CO_2$; flow 5 mL/min at UV 225 nm confirms the enantiomerically enriched (>99% ee) enantiomer with $R_t$=1.01 minutes (175 mg, 360 μmoles). This material (free base, isomer 1) is dissolved in DCM (1 mL) and methanol (0.5 mL) and 1 M hydrogen chloride in diethyl ether (0.36 mL, 360 μmoles) is added. The solvent is removed in vacuo to give the title compound (183 mg, 38%). ES/MS (m/e): 486 (M+H).

Example 4

N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide hydrochloride

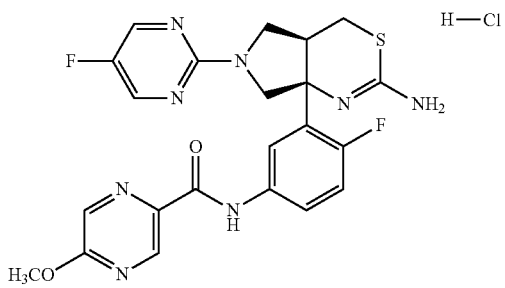 [SMILES: COc1cnc(C(=O)Nc2ccc(F)c([C@]34CN(c5ncc(F)cn5)C[C@H]3CSC(N)=N4)c2)cn1 ; Cl]

N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide (0.350 g, 0.58 mmol, isomer 1) is dissolved in THF (2 mL) and then methanol (4 mL) and ethanol (4 mL) are added. O-Methylhydroxylamine hydrochloride (495 mg, 5.81 mmol) and pyridine (470 µL, 5.81 mmol) are added to the mixture and the reaction is warmed to 50° C. and stirred overnight. Silica gel (~10 g) is added to the reaction and the mixture is concentrated. The sample, dried onto silica gel, is loaded onto an empty cartridge and purified eluting with a 0-10% gradient of 7 N ammonia methanol in DCM. The product is purified a second time on a SCX column using 3:1 DCM:methanol and then 2:1 DCM:7 N ammonia in methanol. The product is purified a final time over silica gel with a 0% to 10% gradient of 7 N ammonia methanol in DCM to give the free base of the title compound. This material is dissolved in DCM (5 mL) and 1 M hydrogen chloride in diethyl ether (0.20 mL, 660 µmol) is added. The solvent is removed in vacuo to give the title compound (71 mg, 23%). ES/MS (m/e): 498 (M+H).

Example 5

Crystalline Form 2 N-[3-[(4aR,7aS)-2-Amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide (hydrated)

Acetonitrile (500 mL) is added to dimethylformamide (19.2 mL, 248.9 mmol). Oxalyl Chloride (39.3 g, 309.63 mmol) followed by 5-methoxypyrazine-2-carboxylic acid (46.0 g, 298.4 mmol) is added to the dimethylformamide solution. In a separate flask, the aqueous solution of (4aR,7aS)-7a-(5-amino-2-fluorophenyl)-6-(5-fluoropyrimidin-2-yl)-4,4a,5,6,7,7a-hexahydropyrrolo[3,4-d][1,3]thiazin-2-amine (56.8 g, 156.75 mmol) is added to acetonitrile (500 mL) and the pH is adjusted to 9 with ammonium hydroxide (95 mL). This mixture is then heated to 50-55° C. The acid chloride solution is added drop wise and the mixture is stirred for 3 hours. The pH is adjusted to 8-9 with ammonium hydroxide. The resulting precipitate is filtered, washed with water, and dried to obtain the title compound (123 g).

The solid is slurried in acetone (250 mL) for 1.5 hours and filtered. The wet cake is washed with acetone to obtain the title compound (110 g with 90.5% purity by HPLC.). THF (1 L) and activated carbon (9 g) are added to the solid and the mixture is heated to reflux overnight. The mixture is filtered through diatomaceous earth and washed with THF (150 mL). The organic solution is concentrated to 10 volumes and heated to 60° C. Water (430 mL) is added and the mixture is stirred at 60° C. for 8 hours. The mixture is cooled to room temperature and stirred for 10 hours. The resulting solid is filtered, washed with THF/water (7:6) and dried to give the title compound (69 g, 88%) LC-MS: m/z=499 (M+1), purity: 98.3%. $^1$H NMR (400 MHz, DMSO-d$_6$) δ ppm 2.99-3.07 (m, 2H) 3.07-3.14 (m, 1H) 3.58-3.67 (m, 1H) 3.68-3.76 (m, 1H) 3.76-3.84 (m, 1H) 4.02 (s, 3H) 4.07 (d, J=10.92 Hz, 1H) 6.08 (s, 2H) 7.19 (dd, J=11.98, 8.72 Hz, 1H) 7.78-7.89 (m, 2H) 8.41 (s, 1H) 8.44 (s, 2H) 8.88 (s, 1H) 10.60 (s, 1H).

X-Ray Powder Diffraction (XRD)

The XRD patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, were adjusted based on NIST 675 standard peaks at 8.853 and 26.774 degrees 2-theta.

A prepared sample of crystalline Form 2 N-[3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide is characterized by an XRD pattern using CuKa radiation as having diffraction peaks (2-theta values) as described in Table 2 below. Specifically, the pattern contains a peak at 11.8°, with one or more peaks selected from the group consisting of 18.6°, 19.3°, and 26.7°; with a tolerance for the diffraction angles of 0.2 degrees.

TABLE 2

X-ray powder diffraction peaks of crystalline Form 2 of Example 5.

| Peak | Angle (2-Theta °) +/− 0.2° | Relative Intensity (% of most intense peak) |
|---|---|---|
| 1 | 11.8 | 100.0 |
| 2 | 18.6 | 71.4 |
| 3 | 19.3 | 45.5 |
| 4 | 26.7 | 41.9 |
| 5 | 20.6 | 27.3 |
| 6 | 9.0 | 19.0 |
| 7 | 24.8 | 18.5 |
| 8 | 22.4 | 15.5 |
| 9 | 31.9 | 14.3 |
| 10 | 10.6 | 11.2 |

Example 6

N-[3-[(4aR,7aS)-2-Amino-6-(5-fluoropyrimidin-2-yl)-4,4a,5,7-tetrahydropyrrolo[3,4-d][1,3]thiazin-7a-yl]phenyl]-5-cyano-pyridine-2-carboxamide hydrochloride

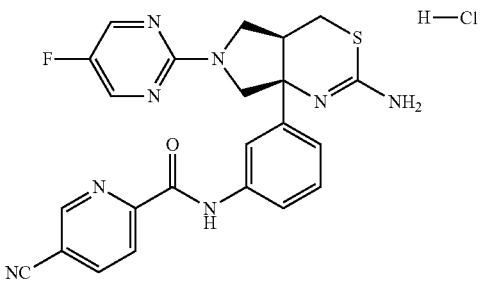 [SMILES: N#Cc1ccc(C(=O)Nc2cccc([C@]34CN(c5ncc(F)cn5)C[C@H]3CSC(N)=N4)c2)nc1 ; Cl]

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-5-cyano-pyridine-2-carboxamide (360 mg, 0.59 mmol) is dissolved in ethanol (10 mL) and DCM (2 mL). 0-Methylhydroxylamine hydrochloride (504 mg, 5.91 mmol) and pyridine (478 µL, 5.91 mmol) are added and the reaction is stirred at room temperature over the weekend (70 hours). The reaction is warmed to 60° C. and stirred for 24 hours. The reaction is concentrated to give the crude product and purified via silica gel chromatography using a 0-10% gradient of 7 N ammonia methanol in DCM to give the free base of the title compound. This material is dissolved in DCM (5 mL) and 1 M hydrogen chloride in diethyl ether (0.54 mL, 540 µmol) is added. The solvent is removed in vacuo to give the title compound (240 mg, 75%). ES/MS (m/e): 475 (M+H).

Example 7

N-[3-[(4aR,7aS)-2-Amino-6-(5-fluoropyrimidin-2-yl)-4,4a,5,7-tetrahydropyrrolo[3,4-d][1,3]thiazin-7a-yl]phenyl]-3,5-difluoro-pyridine-2-carboxamide hydrochloride

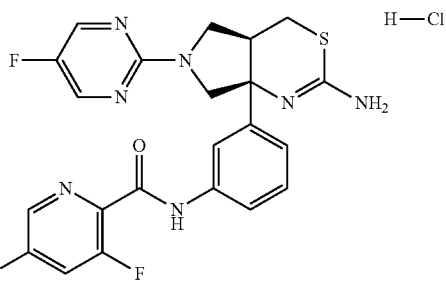

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-3,5-difluoro-pyridine-2-carboxamide (330 mg, 0.53 mmol) is dissolved in THF (10 mL) and diluted with ethanol (10 mL). 0-Methylhydroxylamine hydrochloride (453 mg, 5.32 mmol) and pyridine (430 µL, 5.91 mmol) are added and the reaction is stirred at room temperature over the weekend (70 hours). The reaction is warmed to 60° C. and stirred for 24 hrs. The mixture is concentrated onto silica gel (~10 g) and purified via silica gel chromatography using a 0-10% gradient of 7 N ammonia methanol in DCM to give the free base of the title compound. This material is dissolved in DCM (5 mL) and 1 M hydrogen chloride in diethyl ether (0.49 mL, 490 µmol) is added. The solvent is removed in vacuo to give the title compound (159 mg, 54%). ES/MS (m/e): 486 (M+H).

Example 8

N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-cyano-pyridine-2-carboxamide hydrochloride

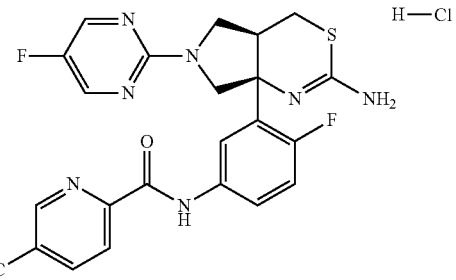

N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-5-cyano-pyridine-2-carboxamide (133 mg, 0.22 mmol, isomer 1) is dissolved in THF (1 mL) and diluted with methanol (3 mL) and ethanol (3 mL). 0-Methylhydroxylamine hydrochloride (190 mg, 2.2 mmol) and pyridine (180 µL, 2.2 mmol) are added. The reaction is warmed to 50° C. and stirred overnight. The mixture is concentrated onto silica gel (~10 g) and purified via silica gel chromatography eluting with a 0-10% gradient of 7 N ammonia methanol in DCM. The material is purified a second time on a SCX column using 3:1 DCM:methanol and then 2:1 DCM:7 N ammonia in methanol. The mixture is purified a final time over silica gel with a 0% to 10% gradient of 7 N ammonia methanol in DCM to give the free base of the title compound. This material is dissolved in DCM (5 mL) and 1 M hydrogen chloride in diethyl ether (0.27 mL, 270 µmol) is added. The solvent is removed in vacuo to give the title compound (114 mg, 97%). ES/MS (m/e): 493 (M+H).

Example 9

N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-3,5-difluoro-pyridine-2-carboxamide hydrochloride

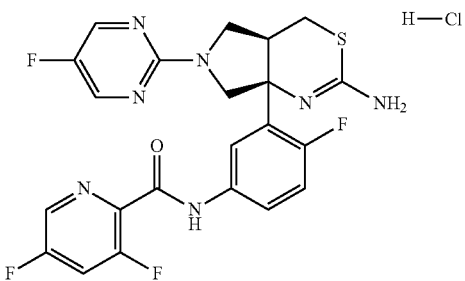 [SMILES: NC1=N[C@@]2(c3cccc(NC(=O)c4ncc(F)cc4F)c3)CN(c3ncc(F)cn3)C[C@H]2CS1 ; Cl]

N-[3-[(4aR,7aS)-2-benzamido-6-(5-fluoropyrimidin-2-yl)-4,4a,5,7-tetrahydropyrrolo[3,4-d][1,3]thiazin-7a-yl]-4-fluoro-phenyl]-3,5-difluoro-pyridine-2-carboxamide (190 mg, 0.31 mmol, isomer 1) is dissolved in THF (1 mL) and diluted with methanol (3 mL) and ethanol (3 mL). O-Methylhydroxylamine hydrochloride (267 mg, 3.1 mmol) and pyridine (253 µL, 3.1 mmol) are added and the reaction is warmed to 50° C. and stirred overnight. The reaction is purified on an SCX column using 3:1 DCM:methanol and then 2:1 DCM:7 N ammonia in methanol. The material is purified a final time over silica gel with a 0% to 10% gradient of 7 N ammonia in methanol in DCM to give the free base of the title compound. This material is dissolved in DCM (5 mL) and 1 M hydrogen chloride in diethyl ether (0.20 mL, 200 µmol) is added. The solvent is removed in vacuo to give the title compound (101 mg, 60%). ES/MS (m/e): 504 (M+H).

Example 10

N-[3-[(4aR,7aS)-2-Amino-6-(5-fluoropyrimidin-2-yl)-4a,5,6,7-tetrahydropyrrolo[3,4-d][1,3]thiazin-7a (4H)-yl]-4-fluoro-phenyl]-3,5-difluoro-pyridine-2-carboxamide

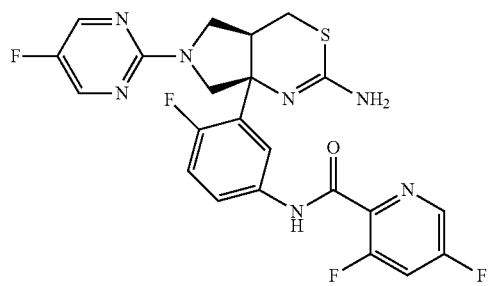 [SMILES: NC1=N[C@@]2(c3cc(NC(=O)c4ncc(F)cc4F)ccc3F)CN(c3ncc(F)cn3)C[C@H]2CS1]

Oxalyl chloride (10.5 ml, 136.4 mmol) is added to a solution of 3,5-difluoropicolinic acid (19.9 g, 125 mmol) in acetonitrile (617 mL) and dimethylformamide (10.5 mL). After 30 minutes stirring, the solution is added to a freshly prepared solution of (4aR,7aS)-7a-(5-amino-2-fluoro-phenyl)-6-(5-fluoropyrimidin-2-yl)-4,4a,5,7-tetrahydropyrrolo[3,4-d][1,3]thiazin-2-amine (41.1 g, 113 mmol) in a mixture ethanol (823 mL)/water (823 mL) previously heated to 50° C. The reaction is maintained at 50° C. for 1 hour. The reaction mixture is cooled to 22° C. and the solvent is evaporated. The aqueous solution is diluted with DCM (1 L), and the pH is adjusted with 2 M sodium hydroxide to pH=11. The organic layer is separated, and the aqueous layer is washed with additional DCM (2×400 mL). The organic extracts are combined, dried over sodium sulfate, filtered and evaporated to dryness. The crude material is purified by silica gel chromatography using a gradient of ammoniated methanol 2 N/DCM from 0-10% DCM to give the title compound as an off white solid (45 g, 78%). ES/MS (m/e): 504 (M+1).

In Vitro Assay Procedures:

For in vitro enzymatic and cellular assays, test compounds are prepared in DMSO to make up a 10 mM stock solution. The stock solution is serially diluted in DMSO to obtain a ten-point dilution curve with final compound concentrations ranging from 10 mM to 0.05 nM in a 96-well round-bottom plate before conducting the in vitro enzymatic and whole cell assays.

In Vitro Protease Inhibition Assays:

Expression of Human BACE1

Human BACE1 (accession number: AF190725) is cloned from total brain cDNA by RT-PCR. The nucleotide sequences corresponding to amino acid sequences #1 to 460 are inserted into the cDNA encoding human $IgG_1$(Fc) polypeptide (See Vasser, et al., *Science*, 286, 735-741 (1999)). This fusion protein of BACE1(1-460) and human Fc, named huBACE1:Fc, is constructed into the pJB02 vector. Human BACE1(1-460):Fc (huBACE1:Fc) is transiently expressed in HEK293 cells. 250 µg cDNA of each construct is mixed with Fugene 6 and added to 1 liter HEK293 cells. Four days after the transfection, conditioned media are harvested for purification.

Purification of huBACE1:Fc huBACE1:Fc is purified by Protein A chromatography. The enzyme is stored at −80° C. in small aliquots.

BACE1 FRET Assay

Serial dilutions of test compounds are prepared as described above. Compounds are further diluted 20× in $KH_2PO_4$ buffer. Ten µL of each dilution is added to each well on row A to H of a corresponding low protein binding black plate containing the reaction mixture (25 µL of 50 mM $KH_2PO_4$, pH 4.6, 1 mM TRITON® X-100, 1 mg/mL Bovine Serum Albumin, and 15 µM of FRET substrate) (See Yang, et. al., *J. Neurochemistry*, 91(6) 1249-59 (2004)). The content is mixed well on a plate shaker for 10 minutes. Fifteen μL of two hundred pM human BACE1(1-460):Fc (See Vasser, et al., *Science*, 286, 735-741 (1999)) in the $KH_2PO_4$ buffer is added to the plate containing substrate and test compounds to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 h. The RFU at the end of incubation is recorded with the same excitation and emission settings used at time 0. The difference of the RFU at time 0 and the end of incubation is representative of the activity of BACE1 under the compound treatment. RFU differences are plotted versus inhibitor concentration and a curve is fitted with a four-parameter logistic equation to obtain the $EC_{50}$ and $IC_{50}$ values. (See Sinha, et al., *Nature*, 402, 537-540 (2000)).

The following exemplified compounds are tested essentially as described above and exhibited the following activity for BACE1:

TABLE 3

| Example # | BACE1 $IC_{50}$ (nM) |
|---|---|
| 1 | 0.610 (±0.0948, n = 8) |
| 2 | 0.482 (±0.0580, n = 6) |
| 3 | 0.603 (±0.0815, n = 7) |
| 4 | 0.615 (±0.101, n = 5) |
| 6 | 0.450 (±0.0911, n = 4) |
| 7 | 0.739 (±0.181, n = 7) |
| 8 | 0.358 |
| 9 | 0.780 (±0.120, n = 6) |

Mean ± SEM;
SEM = standard error of the mean

These data demonstrate that the compounds of Table 3 inhibit purified recombinant BACE1 enzyme activity in vitro.

Whole cell assays for measuring the Inhibition of Beta-Secretase Activity HEK293Swe Whole Cell Assay The routine whole cell assay for the measurement of inhibition of beta-secretase activity utilizes the human embryonic kidney cell line HEK293p (ATCC Accession No. CRL-1573) stably expressing a human APP751 cDNA containing the naturally occurring double mutation Lys651Met652 to Asn651Leu652, commonly called the Swedish mutation (noted HEK293Swe) and shown to overproduce Abeta (Citron, et al., *Nature*, 360, 672-674 (1992)). In vitro Abeta reduction assays have been described in the literature (See Dovey, et al., *Journal of Neurochemistry*, 76, 173-181 (2001); Seubert, et al., *Nature*, 361, 260 (1993); and Johnson-Wood, et al., *Proc. Natl. Acad. Sci. USA*, 94, 1550-1555 (1997)).

Cells (HEK293Swe at $3.5 \times 10^4$ cells/well, containing 200 μL culture media, DMEM containing 10% FBS) are incubated at 37° C. for 4 to 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE1 under such conditions. The 10-point inhibition curve is plotted and fitted with the four-parameter logistic equation to obtain the $EC_{50}$ and $IC_{50}$ values for the Abeta-lowering effect. The following exemplified compounds are tested essentially as described above and exhibited the following activity for Abeta lowering effect:

TABLE 4

| Example | HEK 293 Swe A-beta (1-40) ELISA $IC_{50}$ (nM) | HEK 293 Swe A-beta (1-42) ELISA $IC_{50}$ (nM) |
|---|---|---|
| 1 | 0.619 | 0.437 |
| 2 | 0.324 | 0.289 |
| 3 | 1.26 | 0.299 |
| 6 | 0.0887 | 0.0785 |
| 7 | 0.220 | 0.211 |

These data demonstrate that the compounds of Table 4 inhibit native Abeta production in whole cells.

PDAPP Primary Neuronal Assay

A confirmatory whole cell assay is also run in primary neuronal cultures generated from PDAPP transgenic embryonic mice. Primary cortical neurons are prepared from Embryonic Day 16 PDAPP embryos and cultured in 96 well plates ($15 \times 10^4$ cells/well in DMEM/F12 (1:1) plus 10% FBS). After 2 days in vitro, culture media is replaced with serum free DMEM/F12 (1:1) containing B27 supplement and 2 μM (final) of Ara-C (Sigma, C1768). At day 5 in vitro, neurons are incubated at 37° C. for 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE1 under such conditions. The 10-point inhibition curve is plotted and fitted with the four-parameter logistic equation to obtain the $EC_{50}$ and $IC_{50}$ values for the Abeta-lowering effect. The following exemplified compounds are tested essentially as described above and exhibited the following activity for Abeta lowering effect:

TABLE 5

| Example | PDAPP Neuron A-beta (1-40) ELISA $IC_{50}$ (nM) | PDAPP Neuron A-beta (1-42) ELISA $IC_{50}$ (nM) |
|---|---|---|
| 1 | 0.487 (±0.0946, n = 2) | 0.591 (±0.268, n = 2) |
| 2 | 0.244 | 1.22 (±0.967, n = 2) |
| 3 | 0.481 (±0.371, n = 3) | 0.363 (±0.428, n = 3) |
| 4 | 0.275 (±0.176, n = 4) | 0.228 (±0.244, n = 3) |
| 6 | 0.132 (±0.0717, n = 2) | 0.0813 |
| 7 | 0.279 (±0.0607, n = 2) | 0.308 (±0.115, n = 2) |
| 8 | 0.137 (±0.0697, n = 3) | 0.0725 (±0.0114, n = 2) |
| 9 | 0.309 (±0.206, n = 3) | 0.379 (±0.353, n = 3) |

TABLE 5-continued

| Example | PDAPP Neuron A-beta (1-40) ELISA IC$_{50}$ (nM) | PDAPP Neuron A-beta (1-42) ELISA IC$_{50}$ (nM) |
| --- | --- | --- |

Mean ± SEM; SEM = standard error of the mean

These data demonstrate that the compounds of Table 5 inhibit Abeta production in whole cells In Vivo Inhibition of Beta-Secretase Several animal models, including mouse, guinea pig, dog, and monkey, may be used to screen for inhibition of beta-secretase activity in vivo following compound treatment. Animals used in this invention can be wild type, transgenic, or gene knockout animals. For example, the PDAPP mouse model, prepared as described in Games et al., Nature 373, 523-527 (1995), and other non-transgenic or gene knockout animals are useful to analyze in vivo inhibition of Abeta and sAPPbeta production in the presence of inhibitory compounds. Generally, 2 to 12 month old PDAPP mice, gene knockout mice or non-transgenic animals are administered compound formulated in vehicles, such as corn oil, cyclodextran, phosphate buffers, PHARMASOLVE®, or other suitable vehicles. One to twenty-four hours following the administration of compound, animals are sacrificed, and brains as well as cerebrospinal fluid and plasma are removed for analysis of Abetas, C99, and sAPP fragments. (See May, et al., Journal of Neuroscience, 31, 16507-16516 (2011)).

For standard in vivo pharmacology studies, animals are dosed with various concentrations of compound and compared to a vehicle-treated control group dosed at the same time. For some time course studies, brain tissue, plasma, or cerebrospinal fluid is obtained from selected animals, beginning at time 0 to establish a baseline. Compound or appropriate vehicle is administered to other groups and sacrificed at various times after dosing. Brain tissue, plasma, or cerebrospinal fluid is obtained from selected animals and analyzed for the presence of APP cleavage products, including Abeta peptides, sAPPbeta, and other APP fragments, for example, by specific sandwich ELISA assays. At the end of the test period, animals are sacrificed and brain tissues, plasma, or cerebrospinal fluid are analyzed for the presence of Abeta peptides, C99, and sAPPbeta, as appropriate. Brain tissues of APP transgenic animals may also be analyzed for the amount of beta-amyloid plaques following compound treatment. "Abeta 1-x peptide" as used herein refers to the sum of Abeta species that begin with residue 1 and ending with a C-terminus greater than residue 28. This detects the majority of Abeta species and is often called "total Abeta".

Animals (PDAPP or other APP transgenic or non-transgenic mice) administered an inhibitory compound may demonstrate the reduction of Abeta or sAPPbeta in brain tissues, plasma or cerebrospinal fluids and decrease of beta amyloid plaques in brain tissue, as compared with vehicle-treated controls or time zero controls. Three hours after administration of 1, 3, or 10 mg/kg oral dose of the compound of Example 1 to young female PDAPP mice, Abeta 1-x peptide levels are reduced approximately 34%, 48%, and 53% in brain hippocampus, and approximately 43%, 59% and 66% in brain cortex, respectively, compared to vehicle-treated mice.

Three hours after administration of 1 or 3 mg/kg oral dose of the compound of Example 3, Abeta 1-x peptide levels are reduced approximately 38% and 50% in brain hippocampus, and approximately 34% and 53% in brain cortex, respectively compared to vehicle-treated mice.

For Example 4, 3 hours after administration of 0.3, 1, or 3 mg/kg oral dose of the compound, Abeta 1-x peptide levels are reduced approximately 31%, 39%, and 61% in brain hippocampus, and approximately 28%, 42%, and 64% in brain cortex, respectively compared to vehicle-treated mice.

Given the activity of Examples 1, 3, and 4 against BACE enzyme in vitro, these Abeta lowering effects are consistent with BACE inhibition in vivo, and further demonstrate CNS penetration of Examples 1, 3, and 4.

These studies show that compounds of Examples 1 to 9 inhibit BACE and are, therefore, useful in reducing Abeta levels.

Combination Study

BACE Inhibitor Feeding Pilot Study

A pilot pharmacokinetic and pharmacodynamic study is performed in PDAPP mice fed a chow diet containing a BACE inhibitor, such as a compound of Formula I or pharmaceutically acceptable salt thereof in order to define doses that provide minimal to marked plasma and brain Abeta reduction by BACE inhibition alone. Young PDAPP mice are fed for 14 days a diet containing a chow diet containing the BACE inhibitor at "quasi-bid" equivalent doses of 3 mg/kg, 10 mg/kg, 30 mg/kg, or 100 mg/kg. The BACE inhibitor at ~0.05, 0.15, 0.5, or 1.5 mg per gram of certified rodent diet #8728CM (Harlan labs) is mixed in a Sorvall mixer for 10 minutes and then mixed with Hobart mixer for 15 minutes prior to pelleting. Thirty-two young female PDAPP mice are randomized by parental line into 4 groups of 8 consisting of a vehicle-treatment group and the three doses of BACE inhibitor. Mice are allowed ad libitum access to food for 14 days and subsequently sacrificed. Mice are anesthetized with $CO_2$ and blood collected by cardiac puncture into EDTA-coated microcentrifuge tubes and stored on ice. Subsequently, plasma is collected by centrifugation of blood samples for 4 minutes at 14,000 rpm at room temperature, transferred to untreated microcentrifuge tubes, then frozen on dry ice and stored at −80° C. until analysis. Mice are sacrificed by decapitation, brains are rapidly microdissected into halves, flash frozen on dry ice and stored at −80° C. until analysis (one half for Abeta analysis and the other half for compound exposures measurement). For analysis of parenchymal Abeta, brain samples are homogenized in 5.5 M guanidine-HCl buffer (0.5 mL per half brain) with tissue tearer (model 985-370) at speed 5 for about 1 minute. Homogenized brain samples are nutated overnight at room temperature.

For Abeta ELISA analysis, extracts are collected and diluted at least 1:10 in casein buffer (1×PBS with 0.25% casein, 0.05% Tween 20, 0.1% thimerosal, pH 7.4 with protease inhibitor cocktail (Sigma P9340 at 0.01 mg/mL)) and centrifuged at 14000 rpm for 10 minutes. For analysis of plasma Abeta, samples are diluted 1:2 in specimen buffer (PBS; 0.05% Triton X-405; 0.04% thimerasol, 0.6% BSA), prior to analysis by ELISA. Plasma human $Abeta_{1-x}$ is determined by sandwich ELISA using m266.2 (anti-$Abeta_{13-28}$) and biotinylated 3D6 (anti-Abeta1-5) as the capture and reporter antibodies, respectively. Unknowns are assayed in duplicate and pg/mL determined by interpolating (Soft Max Pro v. 5.0.1, Molecular Dynamics, using 4-parameter fit of the reference curve) from 8 point standard curves and then adjusting for dilution. Parenchymal Abeta is determined by sandwich ELISAs as described above and the values are normalized to protein levels (determined in duplicate by the Bradford Coomassie Plus Protein method) and expressed as pg/mg protein.

To determine the tissue and plasma levels of the BACE inhibitor, the following method is employed: A 0.1 mg/mL stock solution of BACE inhibitor is serially diluted with methanol/water (1:1, v/v), to prepare working solutions, which are then used to fortify control plasma and brain homogenates to yield analyte concentrations of 1, 5, 10, 20, 50, 100, 500, 1000, 2000, 4000, and 5000 ng/mL. Prior to analysis, brain samples are homogenized in 3-volumes of methanol/water (1:4, v/v) with an ultrasonic disrupter. An aliquot of each study sample, appropriate calibration standard and control matrix samples are transferred to a 96-well plate and then mixed with acetonitrile containing internal standard. After mixing, the samples are centrifuged to pellet the precipitated proteins. Aliquots of the resulting supernatants are then transferred to a clean 96-well plate and diluted with methanol/water (1:1, v/v), and 10 microliter aliquots are analyzed by LC-MS/MS. Analyte concentrations are calculated using the response to concentration relationship determined by multiple regression of the calibration curve samples.

In Vivo Combination Study

In order to evaluate combinational plaque lowering therapy of an anti-N3pGlu Abeta monoclonal antibody such as anti-N3pGlu-Abeta monoclonal antibody VII (see Table 1, mE8c-IgG2a; as described in U.S. Pat. No. 8,679,498 B2; U.S. Ser. No. 13/810,895) and a BACE inhibitor, such as a compound of Formula I or a pharmaceutically acceptable salt thereof, a large cohort of PDAPP mice are first aged to 16 to 18-months of age. The aged PDAPP mice are randomized into five treatment arms based upon gender, parental line, and age. There are 20 to 30 aged PDAPP mice per treatment arm. Group 1 is sacrificed as a time zero at study initiation in order to determine the baseline level of pathology prior to therapeutic treatment (necropsy described below). The four remaining groups are then treated as follows: Group-2, control animals receiving placebo chow diet and weekly injections of 12.5 mg/kg of control isotype IgG2a antibody; Group-3, animals receiving weekly injections of 12.5 mg/kg anti-N3pGlu-Abeta monoclonal antibody; Group-4, animals receiving BACE inhibitor chow diet at doses previously defined in the pilot feeding study, but typically ~3 to 30 mg/kg/day; Group-5, animals receiving BACE inhibitor chow diet (~3 to 30 mg/kg/day) and weekly injections of 12.5 mg/kg of anti-N3pGlu-Abetamonoclonal antibody. The anti-N3pGlu-Abeta monoclonal antibody is diluted from sterile stock solutions consisting of the antibody in PBS buffer and is administered to the animals by intraperitoneal injections. The BACE inhibitor is mixed with loose chow diet (~0.15 to 1.5 mg compound per gram of feed depending upon desired dose) and compressed into feed pellets. Animal weight is recorded at study initiation and subsequently weekly for the first month of treatment, and then monthly for the study duration. The food intake is also monitored over the course of the study at regular intervals. The animals receive the study treatments for a total of 4-months. The animals stay on their respective diets until necropsy, which occurs one week after the final antibody injections. At time of necropsy, the animals are anesthetized and blood obtained by cardiac puncture using EDTA pre-rinsed 1 ml syringes. The blood samples are collected on ice and the plasma isolated by standard centrifugation. Subsequently, the animals are perfused with cold heparinized saline and the brain removed and dissected into the left and right hemi-spheres. One brain hemi-sphere is flash frozen and saved for histological analyses. The remaining brain hemi-sphere is dissected into tissue segments consisting of hippocampus, cortex, cerebellum, and mid-brain and subsequently frozen on dry ice. The plasma and tissue samples are stored at −80° C. until time of analysis.

Pharmacokinetic Evaluation

Plasma pharmacokinetics is determined on the plasma samples obtained at time of necropsy. Plasma antibody levels are determined in an antigen binding ELISA assay wherein plates are coated with antigen (Abeta$_{p3-42}$) and subsequently incubated with diluted plasma samples or a reference standard consisting of a serial dilution of the anti-N3pGlu monoclonal antibody in assay buffer (PBS+ control murine plasma). After washing the plate, the bound murine antibody was detected with an anti-murine-HRP conjugated antibody followed by color development with TMB. To determine the tissue (mid-brain) and plasma levels of the BACE inhibitor, the following method is employed: A 0.1 mg/mL stock solution of BACE inhibitor is serially diluted with methanol/water (1:1, v/v), to prepare working solutions, which are then used to fortify control plasma and brain homogenates to yield analyte concentrations of 1, 5, 10, 20, 50, 100, 500, 1000, 2000, 4000, and 5000 ng/mL. Prior to analysis, brain samples are homogenized in 3-volumes of methanol/water (1:4, v/v) with an ultrasonic disrupter. An aliquot of each study sample, appropriate calibration standard and control matrix samples are transferred to a 96-well plate and then mixed with acetonitrile containing internal standard. After mixing, the samples are centrifuged to pellet the precipitated proteins. Aliquots of the resulting supernatants are then transferred to a clean 96-well plate and diluted with methanol/water (1:1, v/v), and 10 microliter aliquots are analyzed by LC-MS/MS. Analyte concentrations are calculated using the response to concentration relationship determined by multiple regression of the calibration curve samples.

Pharmacodynamic Evaluation

The parenchymal Abeta concentrations are determined in guanidine solubilized tissue homogenates by sandwich ELISA. Tissue extraction is performed with the bead beater technology wherein frozen tissue is extracted in 1 ml of 5.5 M guanidine/50 mM Tris/0.5× protease inhibitor cocktail at pH 8.0 in 2 ml deep well dishes containing 1 ml of siliconized glass beads (sealed plates were shaken for two intervals of 3-minutes each). The resulting tissue lysates are analyzed by sandwich ELISA for Abeta$_{1-40}$ and Abeta$_{1-42}$: bead beater samples are diluted 1:10 in 2% BSA/PBS-T and filtered through sample filter plates (Millipore). Samples, blanks, standards, quality control samples, are further diluted in 0.55 M guanidine/5 mM Tris in 2% BSA/PBST prior to loading the sample plates. Reference standard are diluted in sample diluent. Plates coated with the capture antibody 21F12 (anti-Abeta$_{42}$) or 2G3 (anti-Abeta$_{40}$) at 15 µg/ml are incubated with samples and detection is accomplished with biotinylated 3D6 (anti-Abeta$_{1-x}$) diluted in 2% BSA/PBS-T, followed by 1:20 K dilution NeutrAvidin-HRP (Pierce) in 2% BSA/PBS-T and color development with TMB (Pierce). The Abeta levels are interpolated from standard curves and the final tissue concentration is calculated as nanograms of Abeta per milligram of tissue wet weight. The percent area of the hippocampus and cortex occupied by deposited Abeta is determined histologically. Cryostat serial coronal sections (7 to 10 μm thick) are incubated with 10 μg/ml of biotinylated 3D6 (anti-Abeta$_{1-x}$) or negative control murine IgG (biotinylated). Secondary HRP reagents specific for biotin are employed and the deposited Abeta visualized with DAB-Plus (DAKO) Immunoreactive Abeta deposits are quantified in defined areas of interest within the hippocampus or cortex by analyzing captured images with Image Pro plus software (Media Cybernetics).

These studies may show that the combination therapy of an anti-N3pGlu-Abeta monoclonal antibody and a BACE inhibitor, such as a compound of Formula I or pharmaceutically acceptable salt thereof, may result in enhanced Abeta reductions relative to the individual mono-therapies.

```
Sequence Listing
                <SEQ ID NO: 1; PRT1; Artificial>
(LCDR1-B12L/R17L)
KSSQSLLYSRGKTYLN <SEQ ID NO: 2; PRT1; Artificial>
(LCDR2-B12L/R17L)
AVSKLDS <SEQ ID NO: 3; PRT1; Artificial>
(LCDR3-B12L/R17L)
VQGTHYPFT <SEQ ID NO: 4; PRT1; Artificial>
(HCDR1-B12L)
GYDFTRYYIN <SEQ ID NO: 5; PRT1; Artificial>
(HCDR1-R17L)
GYTFTRYYIN <SEQ ID NO: 6; PRT1; Artificial>
(HCDR2-B12L/R17L)
WINPGSGNTKYNEKFKG <SEQ ID NO: 7; PRT1; Artificial>
(HCDR3-B12L)
EGITVY <SEQ ID NO: 8; PRT1; Artificial>
(HCDR3-R17L)
EGTTVY <SEQ ID NO: 9; PRT1; Artificial>
(LCVR-B12L/R17L)
DIVMTQTPLSLSVTPGQPASISCKSSQSLLYSRGKTYLNWLLQKPGQSPQ

LLIYAVSKLDSGVPDRFSGSGSGTDFTLKISRVEAEDVGVYYCVQGTHYP

FTFGQGTKLEIK

<SEQ ID NO: 10; PRT1; Artificial>
(HCVR-B12L)
QVQLVQSGAEVKKPGSSVKVSCKASGYDFTRYYINWVRQAPGQGLEWMGW

INPGSGNTKYNEKFKGRVTITADESTSTAYMELSSLRSEDTAVYYCAREG

ITVYWGQGTTVTVSS

<SEQ ID NO: 11; PRT1; Artificial>
(HCVR-R17L)
QVQLVQSGAEVKKPGSSVKVSCKASGYTFTRYYINWVRQAPGQGLEWMGW

INPGSGNTKYNEKFKGRVTITADESTSTAYMELSSLRSEDTAVYYCAREG

TTVYWGQGTTVTVSS

<SEQ ID NO: 12; PRT1; Artificial>
(LC-B12L/R17L)
DIVMTQTPLSLSVTPGQPASISCKSSQSLLYSRGKTYLNWLLQKPGQSPQ

LLIYAVSKLDSGVPDRFSGSGSGTDFTLKISRVEAEDVGVYYCVQGTHYP

FTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

<SEQ ID NO: 13; PRT1; Artificial>
(HC-B12L)
QVQLVQSGAEVKKPGSSVKVSCKASGYDFTRYYINWVRQAPGQGLEWMGW

INPGSGNTKYNEKFKGRVTITADESTSTAYMELSSLRSEDTAVYYCAREG

ITVYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

<SEQ ID NO: 14; PRT1; Artificial>
(HC-R17L)
QVQLVQSGAEVKKPGSSVKVSCKASGYTFTRYYINWVRQAPGQGLEWMGW

INPGSGNTKYNEKFKGRVTITADESTSTAYMELSSLRSEDTAVYYCAREG

TTVYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG
```

We claim:

1. A method of treating Alzheimer's disease in a patient, comprising administering to a patient in need of such treatment an effective amount of a compound of the formula:

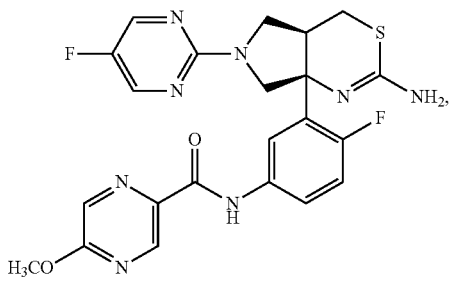 [SMILES: COc1cnc(C(=O)Nc2ccc(F)c([C@]34CN(c5ncc(F)cn5)C[C@H]3CSC(N)=N4)c2)cn1]

or a pharmaceutically acceptable salt thereof, in combination with an effective amount of an anti-N3pGlu Abeta monoclonal antibody.

2. The method according to claim 1 wherein the anti-N3pGlu Abeta monoclonal antibody is B12L or R17L.

3. The method according to claim 2 wherein the anti-N3pGlu Abeta monoclonal antibody is B12L.

4. The method according to claim 3 wherein the compound is N-[3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide.

5. The method according to claim 4 wherein the compound is crystalline Form 2 N-[3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide.

6. The method according to claim 5 wherein the crystalline Form 2 N-[3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide is characterized by a substantial peak in the X-ray diffraction spectrum, at diffraction angle 2-theta of 11.8°, with one or more peaks selected from the group consisting of 18.6°, 19.3°, and 26.7°; with a tolerance for the diffraction angles of 0.2 degrees.

7. The method according to claim 1 wherein the compound and the anti-N3pGlu Abeta monoclonal antibody are administered simultaneously.

8. The method according to according to claim 1 wherein the compound is administered prior to the administration of the anti-N3pGlu Abeta monoclonal antibody.

9. The method according to claim 1 wherein the anti-N3pGlu Abeta monoclonal antibody is administered prior to the administration of the compound.

10. A pharmaceutical composition, comprising a compound of the formula:

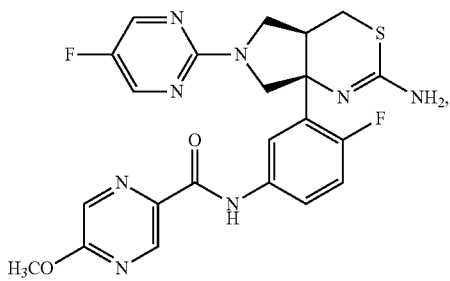 [SMILES: COc1cnc(C(=O)Nc2ccc(F)c([C@]34CN(c5ncc(F)cn5)C[C@H]3CSC(N)=N4)c2)cn1]

or a pharmaceutically acceptable salt thereof, with one or more pharmaceutically acceptable carriers, diluents, or excipients, in combination with a pharmaceutical composition of anti-N3pGlu Abeta monoclonal antibody, with one or more pharmaceutically acceptable carriers, diluents, or excipients.

11. The pharmaceutical composition according to claim 10 wherein the anti-N3pGlu Abeta monoclonal antibody is B12L or R17L.

12. The pharmaceutical composition according to claim 11 wherein the anti-N3pGlu Abeta monoclonal antibody is B12L.

13. The pharmaceutical composition according to claim 12 wherein the compound is N-[3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide.

14. The pharmaceutical composition according to claim 13 wherein the compound is crystalline Form 2 N-[3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide.

15. The pharmaceutical composition according to claim 14 wherein the crystalline Form 2 N-[3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide is characterized by a substantial peak in the X-ray diffraction spectrum, at diffraction angle 2-theta of 11.8°, with one or more peaks selected from the group consisting of 18.6°, 19.3°, and 26.7°; with a tolerance for the diffraction angles of 0.2 degrees.

* * * * *

UNITED STATES PATENT AND TRADEMARK OFFICE
CERTIFICATE OF CORRECTION

PATENT NO. : 9,999,624 B2  
APPLICATION NO. : 15/503027  
DATED : June 19, 2018  
INVENTOR(S) : Patrick Cornelious May and Dustin James Mergott Page 1 of 1

It is certified that error appears in the above-identified patent and that said Letters Patent is hereby corrected as shown below:

On the Title Page (*), Column 1, Line 3, after "0 days." delete "days.".

In the Claims

At Column 75, Line 4, in Claim 8, delete "according to according to" and insert -- according to --, therefor.

Signed and Sealed this  
Eleventh Day of December, 2018

Andrei Iancu  
*Director of the United States Patent and Trademark Office*